United States Patent [19]

Fujii et al.

[11] Patent Number: 5,827,426
[45] Date of Patent: Oct. 27, 1998

[54] LIQUID CHROMATOGRAPH AND LIQUID CHROMATOGRAPHY

[75] Inventors: Yoshio Fujii; Masahito Ito; Hiroshi Satake, all of Hitachinaka, Japan

[73] Assignee: Hitachi, Ltd., Tokyo, Japan

[21] Appl. No.: 711,789

[22] Filed: Sep. 10, 1996

[30] Foreign Application Priority Data

Sep. 14, 1995 [JP] Japan .................................. 7-236697

[51] Int. Cl.$^6$ .................................................... B01D 15/08
[52] U.S. Cl. ............................................ 210/198.2; 210/656
[58] Field of Search .............................. 210/638, 656, 210/198.2; 422/70

[56] References Cited

U.S. PATENT DOCUMENTS 5,236,847  8/1993  Satake et al. ............................. 436/89
5,462,659  10/1995  Saxena et al. ......................... 210/198.2

FOREIGN PATENT DOCUMENTS 64-44848  2/1989  Japan .
1-227959  9/1989  Japan .
2-59428  12/1990  Japan .
3-10076  2/1991  Japan .
4-194750  7/1992  Japan .
4-64584  10/1992  Japan .

*Primary Examiner*—Scott W. Houtteman
*Attorney, Agent, or Firm*—Fay, Sharpe, Beall, Fagan, Minnich & McKee

[57] ABSTRACT

A liquid chromatograph and chromatography which can perform analysis at a higher speed with clearer separation between peaks. The liquid chromatograph comprises a separation column (10), a buffer pump (7) for feeding a plurality of buffers 1, 2, 3 and 4 into the separation column (10), a sampler (9) disposed in a flow path between the buffer pump (7) and the separation column (10) for introducing a sample to be analyzed into the flow path, and a reaction coil (14) for mixing and then reacting amino acids separated by the separation column (10) with a ninhydrin reagent. The separation column is sized so that a ratio (L1/R) of its length L1 to its inner diameter R is not more than 10. The particle size of an ion exchange resin filled in the separation column (10) is selected to be not more than 4 μm.

9 Claims, 10 Drawing Sheets

TIME (min)

LIQUID CHROMATOGRAPH AND LIQUID CHROMATOGRAPHY

BACKGROUND OF THE INVENTION

The present invention relates to a liquid chromatograph and a liquid chromatography which are particularly suitable for high speed analysis.

A liquid chromatograph is often used as an apparatus for analyzing samples. In a liquid chromatograph, a sample is mixed with an effluent, a mixture is separated while flowing through a separation column, and sample components are fixed by referring to a resulting chromatogram.

A liquid chromatograph employs a filling material which is filled in a separation column and selected depending on a sample to be analyzed. Of various filling materials, resin is used for analysis of amino acids or the like. In other words, different sample components adhere to resin in the separation column at different times. This phenomenon produces a chromatogram. A description will now be made for an example in which amino acids are analyzed by selecting resin as a filling material of the separation column.

Amino acid assays are mainly grouped into the standard assay for analyzing about 18 components of amino acids as protein hydrolysate (hereinafter referred to as "standard assay"), and the physiological fluid assay for analyzing amino acid family materials of a physiological fluid (hereinafter referred to as "physiological fluid assay"). Of conventional amino acid analyzing methods and apparatus, those relating to the standard assay are described in, for example, Japanese Laid-open Patent No. 64-44848 and Japanese Patent Publication No. 3-10076 and No. 4-64584, and those relating to the physiological fluid assay are described in, for example, Japanese Patent Publication No. 2-59428 and No. 4-194750.

Amino acid analysis takes a long analyzing time because of many components to be analyzed. Heretofore, the standard assay has taken 30 minutes and the physiological fluid assay 110 to 140 minutes.

An analyzing time of a liquid chromatograph can be shortened by reducing the size of resin particles filled in a separation column. The resin particle size was initially over 10 μm, but has had a tendency to gradually reduce with an increasing demand for high speed analysis. The particle size of resin recently used is 5 μm. Furthermore, resin particles of 4 μm or less are also known.

In an amino acid analyzing apparatus requiring 30 minutes for the standard assay as mentioned above, the apparatus is operated on condition that the particle size of ion exchange resin is 3 μm and the inner diameter of a separation column filled with the ion exchange resin is 4.6 mm, as described in Japanese Laid-open Patent No. 1-227959, for example. Also, when analyzing amino acids by the standard assay in 30 minutes, the buffer flow rate is 0.46 ml/min and the load pressure in that condition is about 110 kgf/cm².

Generally, an analyzing time is almost inversely proportional to a buffer flow rate. In theory, therefore, if the buffer flow rate is increased to 0.55 ml/min, the analyzing time can be cut down to 25 minutes. But the load pressure in that case is raised to about 130 kgf/cm². The limit load pressure of a separation column is different depending on apparatus and a pressure value which is recognized as the limit load pressure is also different depending on assayers. If the column exceeds the limit load pressure, it must be refilled. Assuming here that the limit load pressure is 150 kgf/cm² and the buffer flow rate is set to provide the analyzing time of 25 minutes as stated above, analysis can be performed in an initial period, but the column load pressure is increased with repetition of analyzing cycles. As a result, the column life becomes shorter than in the case of 30-minute analysis.

Accordingly, while the above separation column can perform 25-minute analysis, there arise problems that the column life is shortened and the analysis is not suitable for practical purposes. Another problem is that analysis shorter than 25 minutes is infeasible from relation to the limit load pressure.

The foregoing is basically applied to the physiological fluid assay. However, because the physiological fluid assay employs a buffer having different components and starts at a different temperature as compared with the standard assay, the relationship between flow rate and pressure in the physiological fluid assay is not the same as that in the standard assay and a ratio therebetween rises about 20%.

Further, an increase in analysis speed in a liquid chromatograph can be realized by reducing the length of a separation column. In other words, analysis can be sped up by shortening a period of time during which a sample is held in contact with a filling material of the separation column.

However, the reduced length of the separation column raises a problem of deteriorating the separation ability.

SUMMARY OF THE INVENTION

An object of the present invention is to provide a liquid chromatograph and chromatography which can speed up an analyzing time, while maintaining the column life and resolution.

To achieve the above object, according to the present invention, the particle size of resin filled in a separation column is selected to be not more than 4 μm and a ratio (L1/R) of a length (L1) to an inner diameter (R) of the separation column is selected to be not more than 10.

Preferably, the inner diameter (R) of the separation column is selected to be not less than 5 mm.

Preferably, the inner diameter (R) of the separation column is selected to be not more than 7 mm.

Preferably, the linear speed of a buffer flowing through the separation column is selected to be not more than 36 mm/min.

Also, to achieve the above object, according to the present invention, on an assumption that the inner diameter of a reaction coil used in reaction means for reacting a mixture of a sample and a reaction reagent is r (mm), the length of the reaction coil is L2 (m), and the flow rate of a liquid flowing through the reaction coil is f (ml/min), $(r^4 \cdot L2/f)$ is selected to be not more than $2.5 \times 10^{-3}$ (mm$^4$·m/(ml/min)).

Further, the inner diameter r (mm) of the reaction coil used in the reaction means is selected to be not more than 0.25 mm and the flow rate of the liquid flowing through the reaction coil is selected to be not less than 1.0 ml/min.

Preferably, the linear speed of the liquid flowing through the reaction coil used in the reaction means is selected to be not less than 20 m/min.

The inventors discovered that the case of using a filling material for a separation column with the particle size being not more than 4 μm behaves in a different way in points below from the case of using a filling material with a larger particle size:

(1) An increase in diameter of the separation column improves the separation ability, and (2) If the linear speed of a liquid flowing through the separation column exceeds a certain value, the column life is deteriorated rapidly.

As a result of conducting experiments based on the above findings, it was confirmed that when a ratio of the length (L1) to the inner diameter (R) of the separation column is selected to be not more than 10, the analyzing time can be sped up while maintaining the column life and resolution.

Also, by selecting the inner diameter (R) of the separation column to be not less than 5 mm, high speed analysis of 25 minutes or shorter with the standard assay can be achieved.

By selecting the inner diameter (R) of the separation column to be not more than 7 mm, high speed analysis can be achieved without deteriorating sensitivity.

By selecting the linear speed of a buffer flowing through the separation column to be not more than 36 mm/min, analysis can be performed within a region in which the relationship between the buffer linear speed and the inner pressure of the separation column will not depart from a straight line, and hence the column life can be prolonged.

Further, by selecting $(r^4 \cdot L2/f)$ to be not more than $2.5 \times 10^{-3}$ ($mm^4 \cdot m/(ml/min)$) on an assumption that the inner diameter of a reaction coil used in reaction means is r (mm), the length of the reaction coil is L2 (m), and the flow rate of a liquid flowing through the reaction coil is f (ml/min), separated components can be suppressed from spreading in the reaction coil and analysis free from a reduction in separation rate can be achieved.

By selecting the inner diameter r (mm) of the reaction coil used in the reaction means to be not more than 0.25 mm and selecting the flow rate of the liquid flowing through the reaction coil to be not less than 1.0 ml/min, that element of the effects upon a spread of the separated components in the reaction coil which depends on the inner diameter can be held in a practically allowable range and analysis free from a reduction in separation rate can be achieved.

Additionally, by selecting the linear speed of the liquid flowing through the reaction coil used in the reaction means to be not less than 20 m/min, analysis free from a reduction in separation rate can be achieved.

DESCRIPTION OF PREFERRED EMBODIMENT

Prior to describing one embodiment of the present invention, the principal points of the present invention will be described below.

As stated above, it is thought that an analyzing time is almost inversely proportional to a buffer flow rate. In this respect, it was confirmed from experiments that when the buffer flow rate was gradually increased for speed-up of the analyzing time, the column load pressure started to rise excessively from a certain point and, therefore, the relationship between the buffer flow rate and the column load pressure departed upward from a straight line as shown in FIG. 1.

Figure 1:
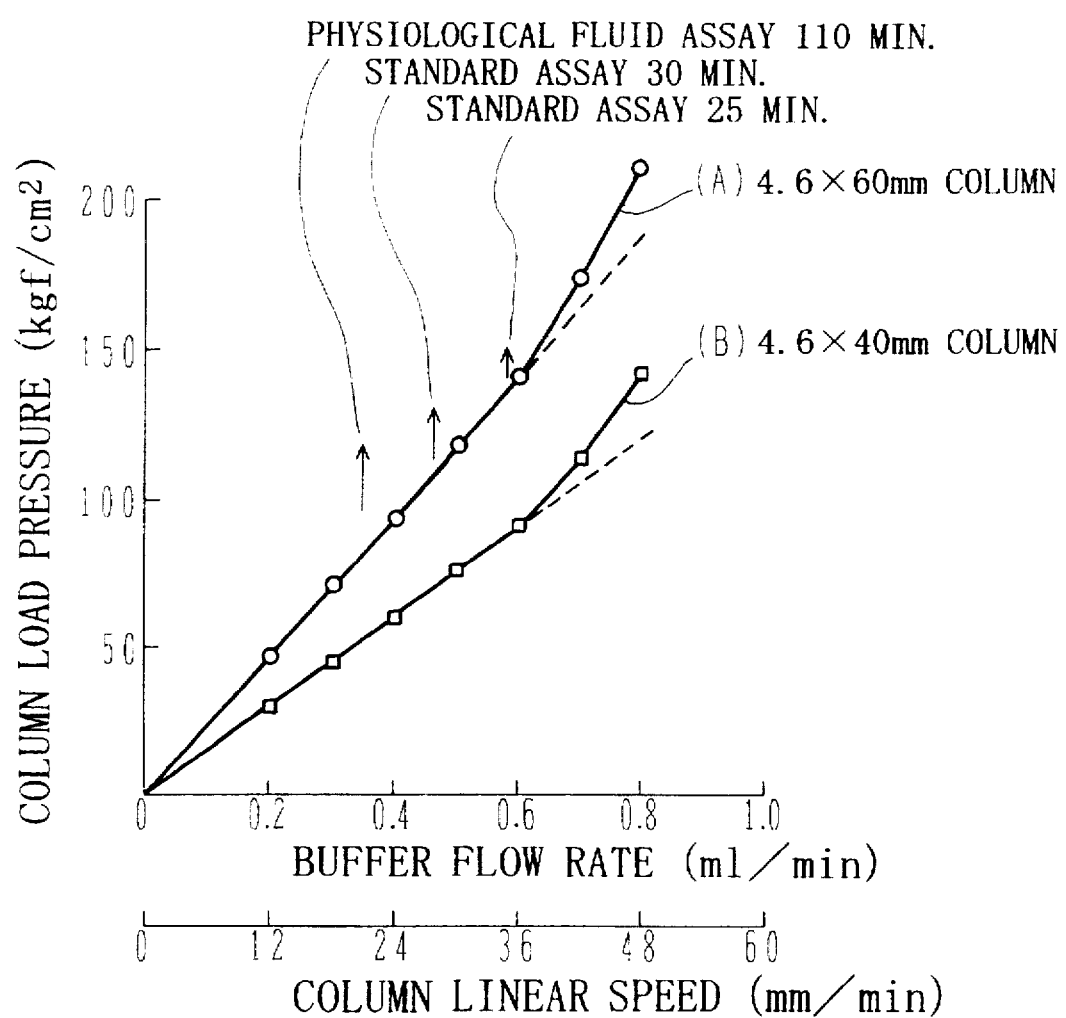
FIG. 1 is a graph for explaining the principal points of the present invention.

In FIG. 1, a line (A) represents the relationship of a column load pressure ($kgf/cm^2$) versus a buffer flow rate resulting when the buffer flow rate was changed to 0.2 ml/min, 0.3 ml/min, 0.4 ml/min, 0.5 ml/min, 0.6 ml/min, 0.7 ml/min and 0.8 ml/min, while using a separation column of 4.6 mm inner diameter and 60 mm length which was employed conventionally. As shown by the line (A) in FIG. 1, the relationship between the buffer flow rate and the column load pressure is linear until the buffer flow rate reaches 0.6 ml/min. It was, however, found that when the buffer flow rate exceeded 0.6 ml/min, the relationship deviated from a linear one. When the buffer flow rate was increased to 0.7 ml/min, the column load pressure became 172 $kgf/cm^2$. This means that the long column life cannot be maintained due to an excessive pressure rise.

Also, a line (B) in FIG. 1 shows results of examining the relationship between a buffer flow rate and a column load pressure when only the column length was changed without changing the column inner diameter. The line (B) of FIG. 1 resulted from measuring the buffer flow rate and the column load pressure by using a separation column of 4.6 mm inner diameter and 40 mm length.

As shown by the line (B) in FIG. 1, it was also found in the separation column of 40 mm length that when the buffer flow rate exceeded 0.6 ml/min, the relationship deviated from a linear one. The column load pressure was 88 $kgf/cm^2$ when the buffer flow rate was 0.6 ml/min, and 112 $kgf/cm^2$ when it was 0.7 ml/min. It was thus confirmed that, comparing the separation column of 60 mm length, the separation column of 40 mm length reached a working limit at a lower column load pressure. Based on this finding, the inventors concluded that a working limit of the column depends not on the column load pressure, but the linear speed of the buffer flowing through the column.

In this connection, when the flow rate of the buffer flowing through the separation column of 4.6 mm inner diameter is 0.6 ml/min, the column linear speed, i.e., the linear speed of the buffer flowing through the same separation column, is 36 mm/min.

Further, it seems that such a phenomenon appears when fine ion exchange resin with the particle size being not more than 4 μm is employed, and hence represents a specific property of the fine ion exchange resin with the particle size being not more than 4 μm. Incidentally, the particle size implies an average particle size and is measured by the particle counting method.

On the basis of the above-stated finding, the inventors made studies on the column size and designed a column with an increased inner diameter in order that the buffer flow rate was raised while keeping to the above-stated limit in the column linear speed. This was deduced from the theoretical concept that by increasing the inner diameter of the separation column, the buffer flow rate can be raised and the analyzing time can be shortened. In addition, since fine resin of particle size being not more than 4 μm was employed to improve the column efficiency, the length of the separation column was reduced to prevent an increase in pressure loss of the separation column that was possibly caused due to the increased buffer flow rate. Then, as a result of studying a ratio (L1/R) of a length L1 to an inner diameter R of the separation column, the ratio was selected to be not more than 10.

Further, even if the separation column as mentioned above is employed to permit high speed analysis and increase a separation rate at the outlet of the separation column, the effect of a spread of the separated components outside the column upon separation is increased due to a flow path line downstream of the separation column.

It was confirmed from experiments that, of flow path parts affecting a spread of the separated components outside the column, the contribution rate of a reaction coil was about 80%. From studies on the effect of the reaction coil upon a spread of the separated components, a spread $\sigma^2$ of the sample zone in the reaction coil is expressed by the Formula 1 below;

$$\sigma^2 = \pi r^4 f L2/24 Dm \qquad \text{(Formula 1)}$$

where r is the radius (mm) of the reaction coil, f is the column flow rate (m³/s), L2 is the length (m) of the reaction coil, and Dm is the diffusion constant of a buffer solute on condition of a laminar flow.

The unit of the spread σ is volume (m³), but the horizontal axis is generally represented by time (s) on a chromatogram. Therefore, assuming a spread of the sample zone in a unit of time to be σ*(s), it is expressed by:

$$\sigma^{*2} = \pi r^4 f L1/24 f d Dm \qquad \text{(Formula 2)}$$

Figure 2:
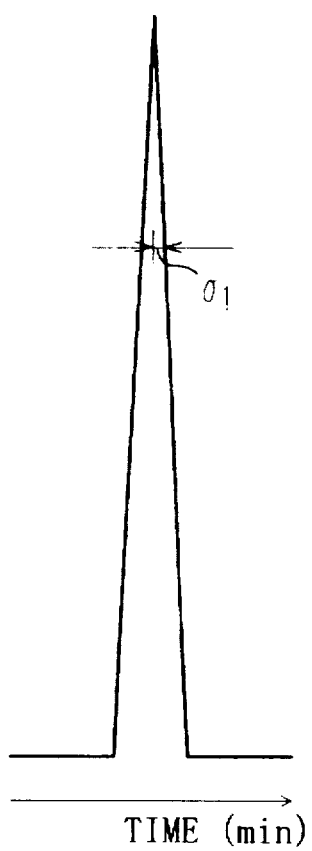
FIG. 2 is a chart for explaining the spread of a chromatogram.

Studying the spread σ* in a unit of time, a chromatogram has a shape as shown in FIG. 2. In FIG. 2, the horizontal axis represents time (min). In such a chromatogram, the standard deviation $\sigma_1$ of a peak is usually on the order of 10 seconds. Accordingly, a square $(\sigma_1)^2$ of the standard deviation $\sigma_1$ of a peak is 100. Thus, if the spread can be held down within 20%, that spread is negligible from the separation point of view.

As a result of determining the spread σ* which satisfies the Formula 3 below, therefore, it is thought that if the spread σ* is made not more than 4 seconds, the spread is negligible from the separation point of view:

$$(\sigma^*)^2 < 0.2 \times 100 \qquad \text{(Formula 3)}$$

Since the unit of time represented by the horizontal axis of a chromatogram is minute (min), the above condition is expressed differently such that the spread σ* should be not more than 0.067 min.

As will be seen from the above Formula 2, the spread σ* in a unit of time is a function of the inner diameter r of the reaction coil, the length L2 thereof, and the column flow rate. Therefore, the condition of $(r^4 \cdot L2)/f$ which is needed to make the spread σ* not more than 0.067 min is given below. Since the diffusion constant Dm is experimentally determined to be $1.20 \times 10^{-9}$ (m²/s), that condition is given as meeting the following Formula 4:

$$(r^4 \cdot L2)/f < 1.5 \times 10^{-7} (m^2/s) \qquad \text{(Formula 4)}$$

The Formula 4 is expressed below in a unit generally used in the field of liquid chromatography:

$$(r^4 \cdot L2)/f < 2.5 \times 10^{-3} (mm^4 \cdot m/(ml/min)) \qquad \text{(Formula 5)}$$

Further, as will be seen from the above Formula 2, the spread σ* in a unit of time is reduced as the flow rate f increases. In other words, when r and L2 are given with fixed values, the effect upon the spread σ* outside the column can be lessened by increasing the flow rate f.

The inner diameter r of reaction coils generally used is in series including 0.25 mm and 0.33 mm. As will be seen from the Formula 2, since the spread σ* in a unit of time is affected by fourth power of the inner diameter r, it is preferable that the inner diameter r be smaller. For this reason, the inner diameter r is selected to be not more than 0.25 mm.

The length L2 of the reaction coil is preferably longer for an improvement in sensitivity because the reaction time is prolonged correspondingly. As will be seen from the Formula 2, however, if the length L2 of the reaction coil is increased, the spread σ* is enlarged. Taking into account the balance between such two contradictory features, the length L2 is selected to be not more than 10 m.

On condition that the inner diameter r and the length L2 of the reaction coil are selected respectively to be not more than 0.25 mm and 10 m as stated above, the flow rate f (ml/min) of the liquid flowing through the column which meets the Formula 5 is determined below:

$$f \geq 2.5 \times 10^{-3} (ml/min)$$

It is thus understood that the flow rate of the liquid flowing through the reaction coil should be selected to satisfy the above condition.

Here, by determining the linear speed of the liquid flowing through the reaction coil under the above condition, it is understood that the linear speed should be not less than 20 (m/min) when the inner diameter r of the reaction coil is 0.25 mm and the flow rate f of the liquid flowing through the column is $2.5 \times 10^{-3}$ (ml/min).

One embodiment of the present invention implemented based on the above-stated principal points of the present invention will be described with reference to FIGS. 3–6, 8 and 9.

Figure 3:
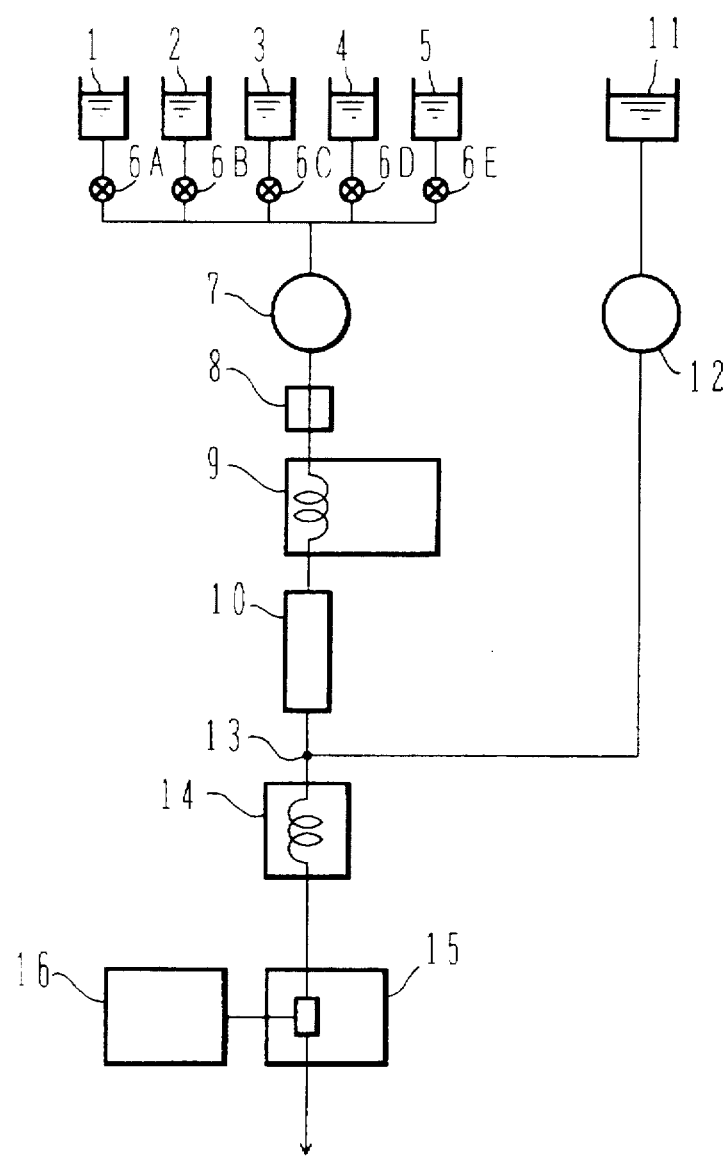
FIG. 3 is a block diagram of an amino acid analyzer according to one embodiment of the present invention.

FIG. 3 is a block diagram of an amino acid analyzer according to one embodiment of the present invention.

A first buffer 1, a second buffer 2, a third buffer 3, a fourth buffer 4 and a column regenerating solution 5 are selected respectively by electrovalves 6A, 6B, 6C, 6D and 6E in sequence, and are sent to an ammonia filter 8 by a buffer pump 7. When sending a buffer mixture which is prepared by mixing, e.g., the second buffer 2 and the third buffer 3 at a predetermined ratio, the electrovalves 6B, 6C are operated to open alternately. Details of this case will be described later.

The buffers, etc. having passed the ammonia filter 8 are then sent to a separation column 10 via an autosampler 9. An amino acid sample introduced by the autosampler 9 is separated into various amino acids in the separation column 10. The separated amino acids are mixed in a mixer 13 with a ninhydrin reagent 11 sent by a ninhydrin pump 12, and thereafter subjected to reactions in a reaction coil 14. The amino acids developing colors as a result of the reactions are continuously detected by a photometer 15 and output in the form of a chromatogram and data by a data processing unit 16 for recording and storage.

Next, the structure of the separation column filled with ion exchange resin will be described with reference to FIG. 4.

Figure 4:
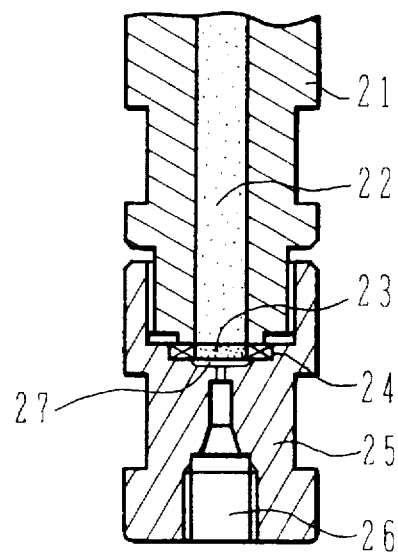
FIG. 4 is a sectional view of a separation column filled with ion exchange resin for use in the amino acid analyzer according to one embodiment of the present invention.

FIG. 4 is a sectional view of the separation column for use in the amino acid analyzer according to one embodiment of the present invention.

Ion exchange resin 22 is filled in a column tube 21. A ring-shaped seal 24 of Teflon and a filter 23 are press-fitted in a column cap 25.

By screwing the column cap 25 onto the column tube 21 after the ion exchange resin 22 has been filled in the column tube 21, the sealing ability of the seal 24 causes the filter 23 to be fast fixed in place and provides the column tube with pressure resistance. Also, the filter 23 is pressed to enter the column tube 21 slightly so that the filled ion exchange resin 22 and the filter 23 are brought into close contact with no gap left therebetween.

Between the filter 23 and the column cap 25, there is defined a filter space 27 in the form of a spot-faced gap. The filter space 27 serves to smooth diffusion of a buffer flow. By providing the filter space 27, flows of separated components are introduced vertically and parallel in the interior of the filter 23 as well, and hence a lowering of resolution is prevented.

The mixer 13 is connected to a connection hole 26 formed in the column cap 25.

A feature of this embodiment is in the configuration of the separation column 10. In a first example explained below, for instance, the separation column 10 is dimensioned is to have an inner diameter (ID) of 6.0 mm and a length of 40 mm.

The reason why the separation column is so dimensioned as follows.

For the conventional separation column (4.6 mmID×60 mm), as stated above, it was confirmed that when the buffer flow rate was gradually increased for speed-up of the analyzing time, the column load pressure started to rise excessively from a certain point and, therefore, the relationship between the buffer flow rate and the column load pressure departed from a linear one. Also, it was experimentally found that the working limit flow rate of the separation column at which the above relationship departed from a linear one was 0.6 ml/min. If it is possible to let the buffer flow at a flow rate higher than that value, the analyzing time can be shortened correspondingly, but the column load pressure becomes so high that the column is not endurable for practical use.

In this connection, the inventors focused an attention on a linear speed of the buffer at such a critical point. The reason is as follows. A separation column of 4.6 mm inner diameter and 40 mm length was experimentally used in expectation of that the limit flow rate would be increased because of the reduced length, i.e., a reduction in load pressure of the separation column. However, the working limit flow rate of the separation column remained the same as 0.6 ml/min in spite of change in column length.

The linear speed of the buffer flowing through the above separation column is 36 mm/min when the buffer flow rate is 0.6 ml/min. In other words, it is thought that a working limit of the separation column depends not on the flow rate but the linear speed of the buffer, and the working limit linear speed of the separation column is 36 mm/min. Thus, the inner diameter of the separation column is increased from 4.6 mm to 6.0 mm from the standpoint of raising the buffer flow rate without exceeding that working limit linear speed.

By so increasing the inner diameter of the separation column, the buffer flow rate can be raised and the analyzing time can be shortened.

Furthermore, if the particle size of the ion exchange resin is selected to be the same 3 μm as conventional for improving the column efficiency, a pressure loss in the column would be increased because of the small particle size. To reduce the pressure loss, therefore, the overall length of the separation column is shortened to 40 mm from 60 mm which has been conventional.

The shortened column length reduces the number of theoretical stages and hence makes a spread of the sample zone outside the column more likely to affect separation. However, this effect can be overcome by suppressing a spread of the sample zone in the reaction coil which contributes to 80% of the spread outside the column.

Based on the concept mentioned above, the relationship between the buffer flow rate and the column load pressure was examined by using the separation column of 6 mm inner diameter and 40 mm length. As a result, the relationship shown in FIG. 5 was confirmed.

Figure 5:
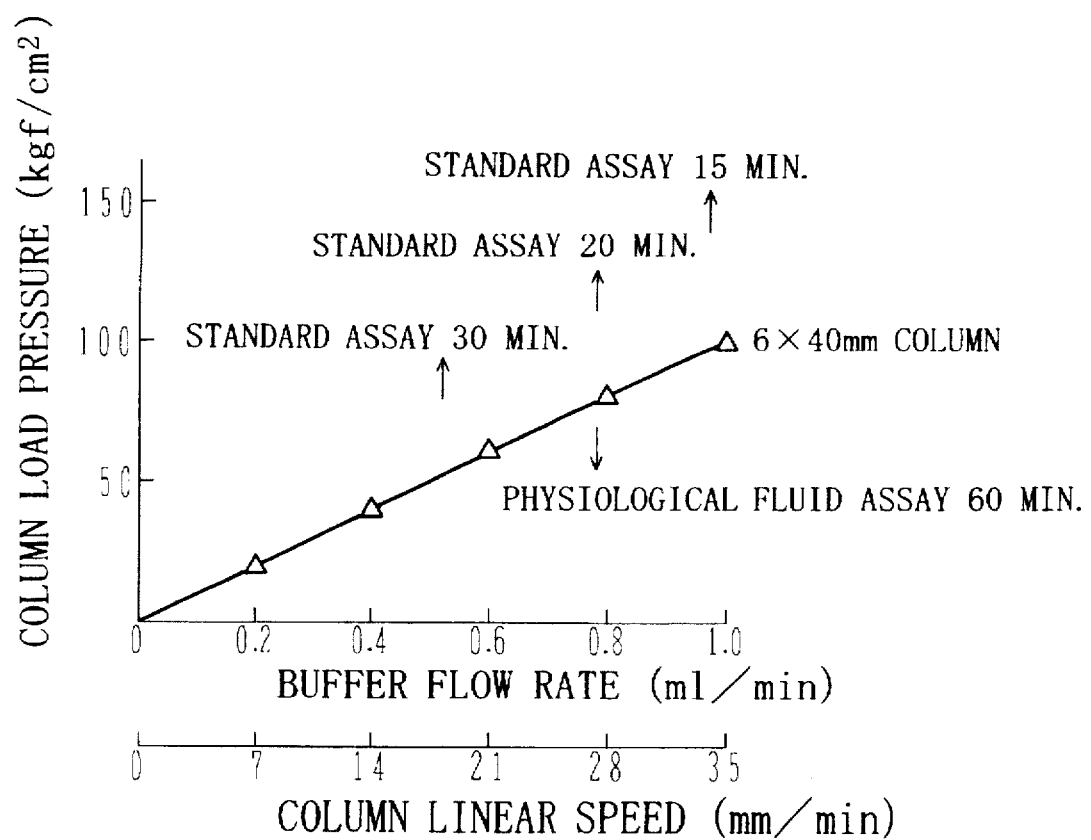
FIG. 5 is a graph showing the relationship between a flow rate of a buffer flowing through the separation column and a column load pressure in the amino acid analyzer according to one embodiment of the present invention.

FIG. 5 is a graph showing the relationship between the buffer flow rate and the column load pressure resulting by using the separation column of 6 mm inner diameter and 40 mm length, filled with ion exchange resin having a particle size of 3 μm, in the amino acid analyzer according to one embodiment of the present invention.

In FIG. 5, the horizontal axis represents a flow rate (ml/min) of the buffer flowing through the separation column and a linear speed (mm/min) of the buffer corresponding to the flow rate, and the vertical axis represents a load pressure (kgf/cm$^2$) of the separation column.

When the buffer flow rate is 0.2 ml/min (the linear speed is 7 mm/min), the load pressure of the separation column is 19 kgf/cm$^2$. When the buffer flow rate is 0.4 ml/min (the linear speed is 14 mm/min), the load pressure of the separation column is 39 kgf/cm$^2$. When the buffer flow rate is 0.6 ml/min (the linear speed is 21 mm/min), the load pressure of the separation column is 58 kgf/cm$^2$. When the buffer flow rate is 0.8 ml/min (the linear speed is 28 mm/min), the load pressure of the separation column is 78 kgf/cm$^2$. When the buffer flow rate is 1.0 ml/min (the linear speed is 35 mm/min), the load pressure of the separation column is 98 kgf/cm$^2$.

It is thus understood that until the buffer flow rate reaches 1.0 ml/min (the linear speed reaches 35 mm/min, there is a linear relationship between the buffer flow rate (the linear speed) and the load pressure of the separation column.

Additionally, the working limit linear speed is 36 mm/min as mentioned above and, even when the buffer flow rate is raised to 1.0 ml/min (the linear speed to 35 mm/min) within that working limit linear speed, the column load pressure is still less; than 100 kgf/cm$^2$. Therefore, the separation column is sufficiently practically usable from the load pressure point of view.

The problem that arises here is a separation rate resulted from raising the buffer flow rate and shortening the analyzing time. This point was studied by carrying out examples as follows. In a first example, the standard assay was carried out with the analyzing time shortened to 20 minutes.

In the first example, the analyzer body employs L-8500 model High Speed Amino Acid Analyzer by Hitachi. The separation column 10 employs Ion Exchange Resin #2622-SC by Hitachi Custom. The particle size of this Ion Exchange Resin #2622-SC by Hitachi Custom is 3 μm. The ammonia filter column 8 employs Ion Exchange Resin #2650L by Hitachi Custom. The reaction coil 14 employs a Teflon tube of 0.25 mm ID (inner diameter)×7 m.

Analytical conditions are as shown in Table 1. For comparison, Table 1 also lists conditions of conventional 30-minute analysis with the standard assay.

TABLE 1

Analytical Conditions of Standard Assay

| Item | Prior Art | Example 1 |
|---|---|---|
| Analyzing time (net) | 30 min | 20 min |
| Column size | 4.6 mmID × 60 mm | 6.0 mmID × 40 mm |
| Particle size of ion exchange resin | 3 μm | 3 μm |
| Buffer flow rate | 0.46 ml/min | 0.78 ml/min |
| Column linear speed | 28 mm/min | 27 mm/min |
| Column load pressure | 110 kgf/cm$^2$ | 80 kgf/cm$^2$ |
| Ninhydrin flow rate | 0.35 ml/min | 0.60 ml/min |
| Reaction coil size | 0.25 mm × 7 m | 0.25 mm × 7 m |
| Reaction coil linear speed | 16.5 m/min | 28.2 m/min |
| Reaction time | 0.42 min | 0.25 min |

Specifically, the separation column has the size of 6.0 mm inner diameter and 40 mm length as described above. In other words, the separation column has a larger inner diameter and a shorter overall length than used in the conventional 30-minute analysis. Further, in the separation column so sized, the ratio (L1/R) of the length L1 to the inner diameter R of the separation column is 6.6, i.e., not more than 10.

Also, the buffer flow rate is selected to 0.78 ml/min so that 20-minute analysis can be achieved with the standard assay. This value of the buffer flow rate is somewhat larger than (30/20) times the buffer flow rate (0.46 ml/min) in the conventional 30-minute analysis. However, the column linear speed, i.e., the linear speed of the buffer flowing through the separation column, is 27 mm/min in the 20-minute analysis of this example and this value is comparable to 28 mm/min in the conventional 30-minute analysis. Since the inner diameter of the separation column is increased while the column linear speed remains almost the same, the buffer flow rate can be raised and hence the analyzing time can be shortened.

Further, since the inner diameter of the separation column is increased while the column linear speed remains almost the same, the load pressure of the separation column becomes 80 kgf/cm$^2$; namely, it can be made lower than 110 kgf/cm$^2$ in the conventional 30-minute analysis. Therefore, if the working limit load pressure is selected to the same value, this example can provide the separation column with longer life.

Corresponding to an increase in the buffer flow rate to 0.78 ml/min, the flow rate of the ninhydrin reagent is increased to 0.60 ml/min.

As to the reaction coil, it has the size of 0.25 mm inner diameter and 7 m length. These values are selected so as to satisfy the above-stated conditions that the inner diameter should be not more than 0.25 mm and the length should be not more than 10 m. The size of the reaction coil itself is the same as that in the conventional 30-minute analysis. The total flow rate of the liquid flowing through the reaction coil, i.e., the sum of the flow rate of the buffer and the flow rate of the ninhydrin reagent is 1.38 ml/min which satisfies the condition that it should be not less than 1.0 ml/min. Incidentally, the total flow rate of the liquid in the conventional 30-minute analysis is 0.81 ml/min.

Also, since a solution mixture of the buffer and the ninhydrin reagent flows through the reaction coil, an increase in both flow rates of the buffer and the ninhydrin reagent also increases the flow rate of the solution mixture. As a result, the linear speed of the solution mixture in the reaction coil is increased from 16.5 m/min to 28.2 m/min which satisfies the condition that it should be not less than 20 m/min.

Additionally, the value of $(r^4 \cdot L2)/f$ becomes $1.24 \times 10^{-3}$ (mm$^4 \cdot$m/(ml/min)) which satisfies the condition that it should be not more than $2.5 \times 10^{-3}$ (mm$^4 \cdot$m/(ml/min)). The spread σ* resulting in this case is 0.047 (min) (=2.8 (s)) which satisfies the condition that it should be not more than 0.067 (min) (=4 (s)).

Because of the increased linear speed of the solution mixture with the reaction coil size remaining the same, the reaction time is shortened to 0.25 minute from 0.42 minute in the conventional 30-minute analysis. While this cutdown of the reaction time reduces sensitivity to some extent, such a lowering of sensitivity is not problematic from the practical point of view. This point will be described later in conjunction with a chromatogram resulting from the 20-minute analysis with the standard assay of this example.

The standard 20-minute analysis can be achieved as described above. But, what attention must be focused on in this connection is a separation rate. Even with speed-up of the analyzing time, the assay is not practicable if the separation rate is reduced. In this example, a satisfactory separation rate is ensured as described later.

The composition of each buffer employed in the standard 20-minute analysis of this example will now be described with reference to Table 2.

TABLE 2

Composition of Buffer for Standard Assay

| Name | PH-1 | PH-2 | PH-3 | PH-4 | PH-RG |
|---|---|---|---|---|---|
| Buffer No. | 1 | 2 | 3 | 4 | 5 |
| Na concentration (N) | 0.08 | 0.2 | 0.2 | 1.2 | 0.2 |
| 1. Distilled water (approx.) | 700 ml | 700 ml | 700 ml | 700 ml | 700 ml |
| 2. Sodium citrate (2H$_2$O) | 3.10 g | 7.74 g | 13.31 g | 26.67 g | — |
| 3. Sodium hydroxide | — | — | — | — | 8.00 g |
| 4. Sodium chloride | 2.83 g | 7.07 g | 3.74 g | 54.35 g | — |
| 5. Citric acid (H$_2$O) | 9.90 g | 22.00 g | 12.80 g | 5.10 g | — |
| 6. Ethyl alcohol | 150.0 ml | 20.0 ml | 4.0 ml | — | 100.0 ml |
| 7. Benzyl alcohol | — | — | — | 5.0 ml | — |
| 8. Thiodiglycol | 5.0 ml | 5.0 ml | 5.0 ml | — | — |
| 9. BRIJ-35* | 4.0 ml | 4.0 ml | 4.0 ml | 4.0 ml | 4.0 ml |
| 10. pH (nominal) | 3.3 | 3.2 | 4.0 | 4.9 | — |
| 11. Total amount (measured) | 1.0 l | 1.0 l | 1.0 l | 1.0 l | 1.0 l |
| 12. Caprylic acid | 0.1 ml | 0.1 ml | 0.1 ml | 0.1 ml | 0.1 ml |

In Table 2, PH-1 represents the composition of the first buffer, PH-2 the composition of the second buffer, PH-3 the composition of the third buffer, PH-4 the composition of the fourth buffer, and PH-RG the composition of the column regenerating solution, respectively.

The first buffer PH-1 has Na concentration of 0.08N and is prepared by dissolving, in distilled water of approximately 700 ml, sodium citrate (2H$_2$O) of 3.10 g, sodium chloride of 2.83 g, citric acid (H$_2$O) of 9.90 g, ethyl alcohol of 150.0 ml, thiodiglycol of 5.0 ml, BRIJ-35 of 4.0 ml and caprylic acid of 0.1 ml, and then further adding distilled water so that the total amount is 1.0 (1000 ml). The pH-value of the first buffer PH-1 is 3.3 (nominal).

The second buffer PH-2 and the third buffer PH-3 have the same composition as the first buffer PH-1, but their composition ratios are changed as shown in Table 2. Thus, the second buffer PH-2 has Na concentration of 0.2N and pH 3.2. Further, the third buffer PH-3 has Na concentration of 0.2N and pH 4.0.

The fourth buffer PH-4 employs benzyl alcohol instead of ethyl alcohol and thioglycol which are employed in the first to third buffers, and has a composition ratio as shown in Table 2. The fourth buffer PH-4 has Na concentration of 1.2N and pH 4.9.

The regenerating solution RH-RG has Na concentration of 0.2N and is prepared by dissolving, in distilled water of approximately 700 ml, sodium hydroxide of 8.00 g, ethyl alcohol of 100.0 ml, BRIJ-35 of 4.0 ml and caprylic acid of 0.1 ml, and then further adding distilled water so that the total amount is 1.01 (1000 ml).

Then, an analysis program showing changeover timing and selection of the buffers for the standard 20-minute analysis this example will be described with reference to Table 3.

TABLE 3

| | | Analysis Program | | | | | |
|---|---|---|---|---|---|---|---|
| STEP | TIME (min) | BUFFER (TOTAL 100%) | | | | | COLUMN TEMP |
| | | V1 | V2 | V3 | V4 | V5 | |
| 1 | 0.0 | 100 | — | — | — | — | 55 |
| 2 | 2.0 | 100 | — | — | — | — | |
| 3 | 2.1 | — | 90 | 10 | — | — | |
| 4 | 4.5 | — | 90 | 10 | — | — | |
| 5 | 4.6 | — | — | 100 | — | — | |
| 6 | 10.0 | — | — | 100 | — | — | |
| 7 | 10.1 | — | — | — | 100 | — | |
| 8 | 17.5 | — | — | — | 100 | — | |
| 9 | 17.6 | — | — | — | — | 100 | |
| 10 | 21.0 | — | — | — | — | 100 | |
| 11 | 21.1 | — | 100 | — | — | — | |
| 12 | 22.0 | — | 100 | — | — | — | |
| 13 | 22.1 | 100 | — | — | — | — | |
| 14 | 23.0 | 100 | — | — | — | — | |

Table 3 represents, from left to right, the step number, the run time (min) of each step, the flow rate of the buffer, and the temperature (°C) of the separation column. In the steps 1–2, i.e., during a period from 0.0 to 2.0 minutes, the electrovalve V1 for introducing the first buffer is driven so that the first buffer flows at 100%. The temperature of the separation column at this time is controlled to 55° C.

In the steps 3–4, i.e., during a period from 2.1 to 4.5 minutes, the electrovalve V2 for introducing the second buffer and the electrovalve V3 for introducing the third buffer are driven so that the second and third buffers flow at a flow rate ratio of 90% and 10%, resulting in 100% in total. The electrovalves V2, V3 are each driven with the pulse width modulation. Thus, the flow rate ratio can be controlled by setting the opening angle of the electrovalve V2 to 90% and the opening angle of the electrovalve V3 to 10%, respectively, closing the electrovalve V3 at the timing at which the electrovalve V2 is opened, and conversely opening the electrovalve V3 at the timing at which the electrovalve V2 is closed. The temperature of the separation column at this time is also controlled to 55° C. Note that, after then, the temperature of the separation column is likewise continuously controlled to 55° C. In a period between the steps 2 and 3, the state of 100% first buffer is gradually changed into the state of 90% second buffer and 10% third buffer with a certain gradient.

In the steps 5–6, i.e., during a period from 4.6 to 10.0 minutes, the electrovalve V3 for introducing the third buffer is driven so that the third buffer flows at 100%. In a period between the steps 4 and 5, the state of 90% second buffer and 10% third buffer is gradually changed into the state of 100% third buffer with a certain gradient.

In the steps 7–8, i.e., during a period from 10.1 to 17.5 minutes, the electrovalve V4 for introducing the fourth buffer is driven so that the fourth buffer flows at 100%. In a period between the steps 6 and 7, the state of 100% third buffer is gradually changed into the state of 100% fourth buffer with a certain gradient.

In the steps 9–10, i.e., during a period from 17.6 to 21.0 minutes, the electrovalve V5 for introducing the regenerating solution is driven so that the regenerating solution flows in 100%. In a period between the steps 8 and 9, the state of 100% fourth buffer is gradually changed into the state of 100% regenerating solution with a certain gradient. Note that the analyzing time is 20 minutes, but the regenerating solution is started to flow from the time of 17.6 minutes, taking into account a delay in the separation column.

In the steps 11–12, i.e., during a period from 21.1 to 22.0 minutes, the electrovalve V2 for introducing the second buffer is driven again so that the second buffer flows in 100%. In a period between the steps 10 and 11, the state of 100% regenerating solution is gradually changed into the state of 100% second buffer with a certain gradient. Here, the second buffer is used to wash away the material residing downstream of the electrovalves.

In the steps 13–14, i.e., during a period from 22.1 to 33.0 minutes, the electrovalve V1 for introducing the first buffer is driven again so that the first buffer flows in 100%. In a period between the steps 12 and 13, the state of 100% second buffer is gradually changed into the state of 100% first buffer with a certain gradient. Here, the first buffer is used to be filled in the flow path line to establish an equilibrium state in the column for preparation of the next measurement cycle.

Figure 6:
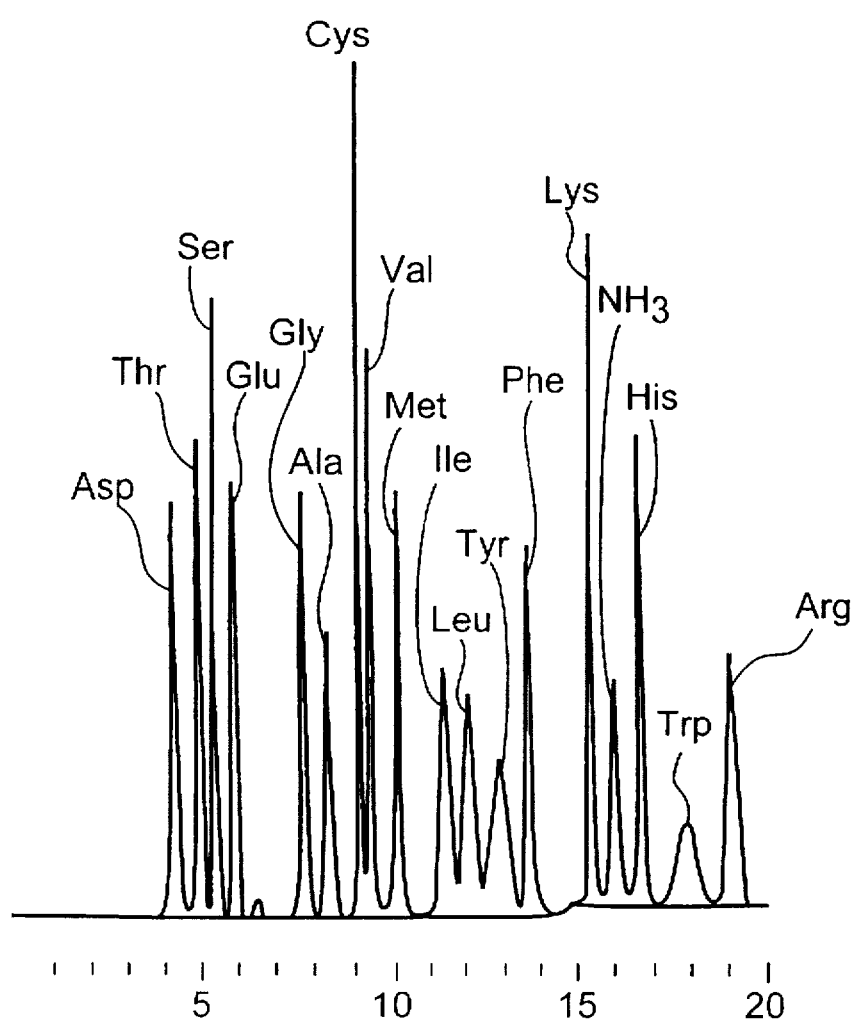
FIG. 6 is a chart; showing a chromatogram resulting when a 20-minute analysis with the standard assay was carried out by using the amino acid analyzer according to one embodiment of the present invention.
Figure 7:
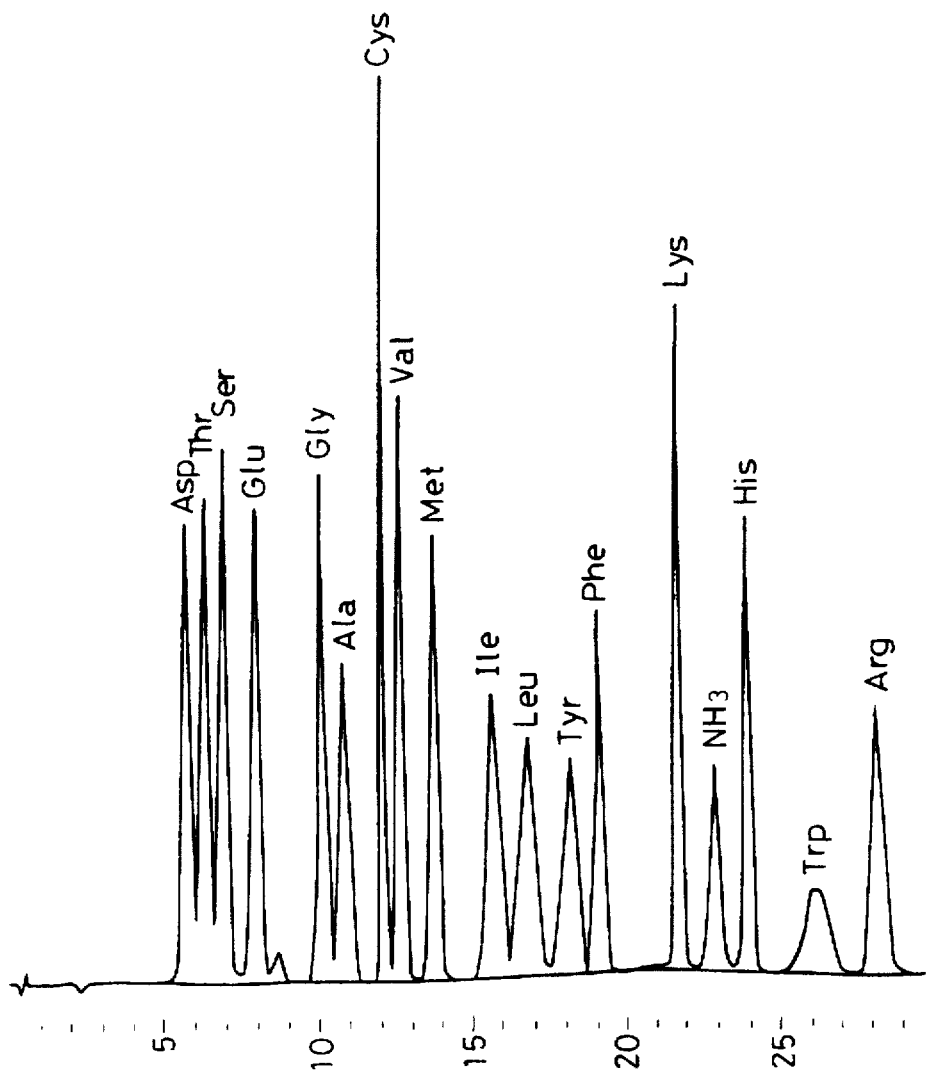
FIG. 7 is a chart showing a chromatogram resulting from conventional 30-minute analysis with the standard assay.

FIG. 6 shows a chromatogram resulted when 18 components of amino acids as protein hydrolysate contained in a standard sample were analyzed according to this example, and FIG. 7 shows a chromatogram resulted when the conventional 30-minute analysis with the standard assay was carried out on the same standard sample. The horizontal axis of each of FIGS. 6 and 7 represents time (min).

As seen from FIG. 6, the analysis of the 18 components is completed in 20 minutes. On the other hand, the conventional standard 30-minute analysis shown in FIG. 7 takes 30 minutes until completion of the analysis. Thus, according to this example, the analysis of the 18 components can be performed at a higher speed, i.e., in 20 minutes, with the standard assay.

As is apparent from comparing FIGS. 6 and 7, during a period from Asp (asparagic acid) to Ala (alanine), this example provides clearer separation between chromatogram peaks than the prior art. As indices for representing a degree of separation between chromatogram peaks, there are generally employed a separation rate of Thr (threonine)— Ser (serine) and a separation rate of Gly (glycine)—Ala (alanine). Table 4 shows calculated separation rates of chromatogram peaks in FIGS. 6 and 7 for those separation rates as indices.

TABLE 4

Comparison of Separation Rates by Standard Assay

|  | Prior Art 30-minute analysis | Example 1 20-minute analysis | Example 2 20-minute analysis | Example 3 20-minute analysis |
|---|---|---|---|---|
| Thr—Ser | 89% | 99% | 91% | 90% |
| Gly—Ala | 95% | 100% | 99% | 98% |

While the separation rate of Thr (threonine)—Ser (serine) is 89% by the conventional standard 30-minute analysis shown in FIG. 7, it is improved to 99% in this example. Also, while the separation rate of Gly (glycine)—Ala (alanine) is 95% by the conventional standard 30-minute analysis, it is improved to 100% in this example.

Stated otherwise, as is apparent from comparing FIGS. 6 and 7, this example makes it possible to speed up the standard assay to 20 minutes, and achieve higher separation rates than by the conventional standard 30-minute analysis.

Incidentally, Example 2 in Table 4 will be described later.

Furthermore, the height of each chromatogram peak is somewhat lower in FIG. 6 representing this example. The reason is that because the flow rates of the buffer and the ninhydrin reagent are increased as shown in Table 1, the linear speed of the solution mixture flowing through the reaction coil is increased and hence the reaction time is shortened to 0.25 minutes from 0.42 minutes in the prior art. However, since the amino acid components under analysis are quantified by the chromatogram peak area method, the effect of a reduction in the peak height is small. The peak area is rather determined more precisely because of the improved separation rate of the chromatogram peak and hence clearer separation between two peaks. As a result, the measurement accuracy is not deteriorated in this example.

According to this example described above, the 20-minute analysis with the standard assay which has been infeasible heretofore can be achieved.

Also, the separation rate is improved as compared with the conventional standard 30-minute analysis.

Further, the load pressure of the separation column is lower than in the conventional standard 30-minute analysis and, therefore, the column life can be prolonged.

Next, a second example of the present invention will be described. This example also intends to achieve 20-minute analysis with the standard assay.

In this second example, too, an amino acid analyzer constructed as shown in FIG. 3 and a separation column having the structure as shown in FIG. 4 are used.

The analyzer body employs L-8500 model High Speed Amino Acid Analyzer by Hitachi. The separation column employs Ion Exchange Resin #2622-SC by Hitachi Custom. The particle size of this Ion Exchange Resin #2622-SC by Hitachi Custom is 3 μm. The ammonia filter column 8 employs Ion Exchange Resin #2650L by Hitachi Custom.

Analytical conditions are as shown in Table 5 below.

TABLE 5

Analytical Conditions of Standard Assay

| Item | Example 2 | Example 3 |
|---|---|---|
| Analyzing time (net) | 20 min | 20 min |
| Column size | 6.0 mmID × 30 mm | 5.0 mmID × 50 mm |
| Particlesize of ion exchange resin | 3 μm | 3 μm |

TABLE 5-continued

Analytical Conditions of Standard Assay

| Item | Example 2 | Example 3 |
|---|---|---|
| Buffer flow rate | 0.59 ml/min | 0.68 ml/min |
| Column linear speed | 21 mm/min | 35 mm/min |
| Column load pressure | 50 kgf/cm$^2$ | 110 kgf/cm$^2$ |
| Ninhydrin flow rate | 0.50 ml/min | 0.55 ml/min |
| Reaction coil size | 0.25 mm × 7 m | 0.25 mm × 7 m |
| Reaction coil linear speed | 22.3 m/min | 25.2 m/min |
| Reaction time | 0.33 min | 0.29 min |

Specifically, the separation column has the size of 6.0 mm inner diameter and 30 mm length as listed above. In other words, the separation column has the same inner diameter as in Example 1, but a shorter length than in Example 1. Further, in the separation column so sized, the ratio (L1/R) of the length L1 to the inner diameter R of the separation column is 5.0, i.e., not more than 10.

Also, the buffer flow rate is selected to 0.59 ml/min so that a 20-minute analysis can be achieved with the standard assay. This value of the buffer flow rate is about ¾ of that in Example 1; namely, it is reduced corresponding to the shorter length of the separation column. However, that value is larger than 0.46 ml/min in the prior art so that the analyzing time can be shortened. As to the linear speed of the buffer flowing through the column, the working limit linear speed is 36 mm/min as stated above and the value of 21 mm/min in this example is within the working limit linear speed.

Further, since the column linear speed is reduced as compared with Example 1, the load pressure of the separation column becomes 50 kgf/cm$^2$; namely, it can be made lower than in the 20-minute analysis of Example 1. Therefore, if the working limit load pressure is selected to the same value, this example can provide the separation column with longer life.

The reaction coil itself has the size of 0.25 mm inner diameter and 7 m length. The total flow rate of the liquid flowing through the reaction coil is 1.09 ml/min which satisfies the condition that it should be not less than 1.0 ml/min.

Also, since a solution mixture of the buffer and the ninhydrin reagent flows through the reaction coil, the linear speed of the solution mixture in the reaction coil is 22.3 m/min which satisfies the condition that it should be not less than 20 m/min.

Additionally, the value of $(r^4 \cdot L2)/f$ becomes $1.57 \times 10^{-3}$ (mm$^4$·m/(ml/min)) which satisfies the condition that it should be not more than $2.5 \times 10^{-3}$ (mm$^4$·m/(ml/min)). The spread σ* resulted in this case is 0.054 (min) (=3.2 (s)) which satisfies the condition that it should be not more than 0.067 (min) (=4 (s)).

Because of the reduced linear speed of the solution mixture with the reaction coil size remained the same, the reaction time is extended to 0.33 minute from 0.25 minute in Example 1. As a result, sensitivity is increased to some extent.

The standard 20-minute analysis can be achieved as described above. But, what attention must be focused on in this connection is a separation rate. Even with speed-up of the analyzing time, the assay is not practicable if the separation rate is reduced. In this example, a satisfactory separation rate is ensured as described later.

The composition of each buffer employed in the standard 20-minute analysis of this example is the same as in Example 1, and the same buffers and regenerating solution as stated above with reference to Table 2 are employed.

Then, an analysis program showing changeover timing and selection of the buffers for the standard 20-minute analysis of this example is the same as used in Example 1, i.e., the analysis program described above with reference to Table 3.

Results obtained from determining a chromatogram in accordance with the analysis program and calculating the separation rates of peaks are as shown in Table 4 above.

More specifically, while the separation rate of Thr (threonine)—Ser (serine) is 89% by the conventional standard 30-minute analysis shown in FIG. 7, it is improved to 91% in this example. Also, while the separation rate of Gly (glycine)—Ala (alanine) is 95% by the conventional standard 30-minute analysis, it is improved to 99% in this example.

Stated otherwise, this example makes it possible to speed up the standard assay to 20 minutes, and achieve higher separation rates than by the conventional standard 30-minute analysis.

Incidentally, as is apparent from the comparison shown in Table 4, while the separation rate of Thr (threonine)—Ser (serine) is improved to 99% by the standard 20-minute analysis of Example 1, it is 91% in this example. Also, while the separation rate of Gly (glycine)—Ala (alanine) is improved to 100% by the standard 20-minute analysis of Example 1, it is 99% in this example. Thus, the separation rate in this example is lower than in Example 1.

This is a result of slowing down the buffer flow rate. In spite of a slight reduction, the separation rate in this example is still higher than in the prior art.

According to this example described above, the 20-minute analysis with the standard assay which has been infeasible heretofore can be achieved.

Also, the separation rate is improved as compared with the conventional standard 30-minute analysis.

Further, the load pressure of the separation column is lower than in the conventional standard 30-minute analysis and, therefore, the column life can be prolonged.

Next, a third example of the present invention will be described. This example also intends to achieve 20-minute analysis with the standard assay.

In this third example, too, an amino acid analyzer constructed as shown in FIG. 3 and a separation column having the structure as shown in FIG. 4 are used.

The analyzer body employs L-8500 model High Speed Amino Acid Analyzer by Hitachi. The separation column employs Ion Exchange Resin #2622-SC by Hitachi Custom. The particle size of this Ion Exchange Resin #2622-SC by Hitachi Custom is 3 µm. The ammonia filter column 8 employs Ion Exchange Resin #2650L by Hitachi Custom.

Analytical conditions are as shown in Table 5 above. Specifically, the separation column has the size of 5.0 mm inner diameter and 50 mm length as listed above. In other words, the separation column has a smaller diameter and a longer length than in Example 1. Further, in the separation column so sized, the ratio (L1/R) of the length L1 to the inner diameter R of the separation column is 10.0, i.e., not more than 10.

Also, the buffer flow rate is selected to 0.68 ml/min so that 20-minute analysis can be achieved with the standard assay. The linear speed of the buffer flowing through the column in this case is 35 mm/min. Since the working limit linear speed is 36 mm/min, the value of 35 mm/min in this example is within the working limit linear speed. Thus, the buffer flow rate is set in this example so that the column linear speed falls within its working limit.

Further, since the column linear speed is increased as compared with Example 1, the load pressure of the separation column becomes 110 kgf/cm$^2$; namely, it is higher than in the 20-minute analysis of Example 1, but the same as in the prior art. Therefore, the column life comparable to that in the prior art is provided.

The reaction coil itself has the size of 0.25 mm inner diameter and 7 m length. The total flow rate of the liquid flowing through the reaction coil is 1.23 ml/min which satisfies the condition that it should be not less than 1.0 ml/min.

Also, since a solution mixture of the buffer and the ninhydrin reagent flows through the reaction coil, the linear speed of the solution mixture in the reaction coil is 25.2 m/min which satisfies the condition that it should be not less than 20 m/min.

Additionally, the value of $(r^4 \cdot L2)/f$ becomes $1.39 \times 10^{-3}$ (mm$^4 \cdot$m/(ml/min)) which satisfies the condition that it should be not more than $2.5 \times 10^{-3}$ (mm$^4 \cdot$m/(ml/min)). The spread σ* resulted in this case is 0.050 (min) (=3.0 (s)) which satisfies the condition that it should be not more than 0.067 (min) (=4 (s)).

Because of the reduced linear speed of the solution mixture with the reaction coil size remained the same, the reaction time is extended to 0.29 minute from 0.25 minute in Example 1. As a result, sensitivity is increased to some extent.

The standard 20-minute analysis can be achieved as described above. But, what attention must be focused on in this connection is a separation rate. Even with speed-up of the analyzing time, the assay is not practicable if the separation rate is reduced. In this example, a satisfactory separation rate is ensured as described later.

The composition of each buffer employed in the standard 20-minute analysis of this example is the same as in Example 1, and the same buffers and regenerating solution as stated above with reference to Table 2 are employed.

Then, an analysis program showing changeover timing and selection of the buffers for the standard 20-minute analysis of this example is the same as used in Example 1, i.e., the analysis program described above with reference to Table 3.

Results obtained from determining a chromatogram in accordance with the analysis program and calculating the separation rates of peaks are as shown in Table 4 above.

More specifically, while the separation rate of Thr (threonine)—Ser (serine) is 89% by the conventional standard 30-minute analysis shown in FIG. 7, it is improved to 90% in this example. Also, while the separation rate of Gly (glycine)—Ala (alanine) is 95% by the conventional standard 30-minute analysis, it is improved to 98% in this example.

Stated otherwise, this example makes it possible to speed up the standard assay to 20 minutes, and achieve higher separation rates than by the conventional standard 30-minute analysis.

Incidentally, as is apparent from comparison shown in Table 4, while the separation rate of Thr (threonine)—Ser (serine) is improved to 99% by the standard 20-minute analysis of Example 1, it is 90% in this example. Also, while the separation rate of Gly (glycine)—Ala (alanine) is improved to 100% by the standard 20-minute analysis of Example 1, it is 98% in this example. Thus, the separation rate in this example is lower than in Example 1.

This is a result of slowing down the buffer flow rate. In spite of a slight reduction, the separation rate in this example is still higher than in the prior art.

According to this example described above, the 20-minute analysis with the standard assay which has been infeasible heretofore can be achieved.

Also, the separation rate is improved as compared with the conventional standard 30-minute analysis.

Further, the load pressure of the separation column is equal to that in the conventional standard 30-minute analysis and, therefore, the comparable column life can be obtained.

Next, a fourth example of the present invention will be described. This example intends to achieve 15-minute analysis with the standard assay.

In this fourth example, too, an amino acid analyzer constructed as shown in FIG. 3 and a separation column having the structure as shown in FIG. 4 are used.

The analyzer body employs L-8500 model High Speed Amino Acid Analyzer by Hitachi. The separation column employs Ion Exchange Resin #2622-SC by Hitachi Custom. The particle size of this Ion Exchange Resin #2622-SC by Hitachi Custom is 3 μm. The ammonia filter column 8 employs Ion Exchange Resin #2650L by Hitachi Custom.

Analytical conditions are as shown in Table 6. For comparison, Table 6 also lists the conditions of the 20-minute analysis with the standard assay shown in Example 1.

TABLE 6

Analytical Conditions of Standard Assay

| Item | Example 4 | Example 1 |
|---|---|---|
| Analyzing time (net) | 15 min | 20 min |
| Column size | 6.0 mmID × 40 mm | 6.0 mmID × 40 mm |
| Particle size of ion exchange resin | 3 μm | 3 μm |
| Buffer flow rate | 0.97 ml/min | 0.78 ml/min |
| Column linear speed | 35 mm/min | 27 mm/min |
| Column load pressure | 100 kgf/cm$^2$ | 80 kgf/cm$^2$ |
| Ninhydrin flow rate | 0.80 ml/min | 0.60 ml/min |
| Reaction coil size | 0.25 mm × 7 m | 0.25 mm × 7 m |
| Reaction coil linear speed | 35.1 m/min | 28.2 m/min |
| Reaction time | 0.19 min | 0.25 min |

Specifically, the separation column has the size of 6.0 mm inner diameter and 40 mm length as listed above. In other words, the separation column has the same size as in Example 1. Further, in the separation column so sized, the ratio (L1/R) of the length L1 to the inner diameter R of the separation column is 6.6, i.e., not more than 10.

Also, the buffer flow rate is selected to 0.97 ml/min so that 15-minute analysis can be achieved with the standard assay. This value of the buffer flow rate is somewhat smaller than (20/15) times the buffer flow rate (0.78 ml/min) in the 20-minute analysis of Example 1. The linear speed of the buffer flowing through the separation column is 35 mm/min in the 15-minute analysis of this example and this value is larger than 28 mm/min in the conventional 30-minute analysis. But since the inner diameter of the separation column is increased as compared with the prior art, the buffer flow rate can be raised and hence the analyzing time can be shortened. In addition, as to the column linear speed, the working limit linear speed is 36 mm/min as stated above and the value of 35 mm/min in this example is within the working limit linear speed.

Further, since the column linear speed is increased as compared with Example 1, the load pressure of the separation column becomes 100 kgf/cm$^2$; namely, it is higher than in the 20-minute analysis of Example 1, but lower than 110 kgf/cm$^2$ in the conventional 30-minute analysis. Therefore, if the working limit load pressure is selected to the same value, this example can provide the separation column with longer life.

Corresponding to an increase in the buffer flow rate to 0.97 ml/min, the flow rate of the ninhydrin reagent is increased to 0.80 ml/min.

The reaction coil itself has the size of 0.25 mm inner diameter and 7 m length. The total flow rate of the liquid flowing through the reaction coil is 1.77 ml/min which satisfies the condition that it should be not less than 1.0 ml/min.

Also, since a solution mixture of the buffer and the ninhydrin reagent flows through the reaction coil, an increase in both flow rates of the buffer and the ninhydrin reagent also increases the flow rate of the solution mixture. As a result, the linear speed of the solution mixture in the reaction coil is 35.1 m/min which satisfies the condition that it should be not less than 20 m/min.

Additionally, the value of $(r^4 \cdot L2)/f$ becomes $9.66 \times 10^{-4}$ (mm$^4 \cdot$m/(ml/min)) which satisfies the condition that it should be not more than $2.5 \times 10^{-3}$ (mm$^4 \cdot$m/(ml/min)). The spread σ* resulted in this case is 0.042 (min) (=2.5 (s)) which satisfies the condition that it should be not more than 0.067 (min) (=4 (s)).

Because of the increased linear speed of the solution mixture with the reaction coil size remained the same, the reaction time is shortened to 0.19 minute from 0.25 minute in Example 1. While this cutdown of the reaction time reduces sensitivity to some extent, such a lowering of sensitivity is not problematic from the practical point of view. This point will be described later in conjunction with a chromatogram resulted by the 15-minute analysis with the standard assay of this example.

The standard 15-minute analysis can be achieved as described above. But, what attention must be focused on in this connection is a separation rate. Even with speed-up of the analyzing time, the assay is not practicable if the separation rate is reduced. In this example, a satisfactory separation rate is ensured as described later.

The composition of each buffer employed in the standard 15-minute analysis of this example is the same as in Example 1, and the same buffers and regenerating solution as stated above with reference to Table 2 are employed.

Then, an analysis; program showing changeover timing and selection of the buffers for the standard 20-minute analysis of this example is the same as used in Example 1, i.e., the analysis program described above with reference to Table 3.

Figure 8:
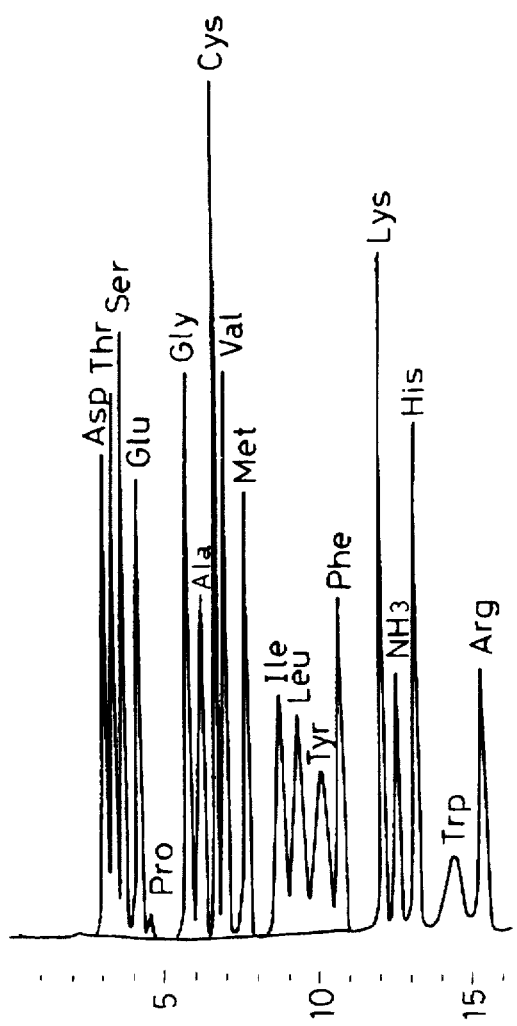
FIG. 8 is a chart showing a chromatogram resulting when a 15-minute analysis with the standard assay was carried out by using the amino acid analyzer according to one embodiment of the present invention.

FIG. 8 shows a chromatogram resulted when 18 components of amino acids as protein hydrolysate contained in a standard sample were analyzed according to this example.

The horizontal axis of FIG. 8 represents time (min). The scale of the time base is the same as in FIG. 6 for Example 1.

As seen from FIG. 8, the analysis of the 18 components is completed in 15 minutes. Thus, according to this example, the analysis of the 18 components can be performed at a higher speed, i.e., in 15 minutes, with the standard assay.

As is apparent from comparing FIG. 8 and FIG. 7 which shows the chromatogram by the prior art, during a period from Asp (asparagic acid) to Ala (alanine), this example provides clearer separation between chromatogram peaks than in the prior art. As indices for representing a degree of separation between chromatogram peaks, there are generally employed a separation rate of Thr (threonine)—Ser (serine) and a separation rate of Gly (glycine)—Ala (alanine). Table 7 shows calculated separation rates of chromatogram peaks in FIG. 7 for those separation rates as indices.

TABLE 7

Comparison of Separation Rates by Standard Assay

|  | Prior Art 30-minute analysis | Example 1 20-minute analysis | Example 4 15-minute analysis |
|---|---|---|---|
| Thr—Ser | 89% | 99% | 93% |
| Gly—Ala | 95% | 100% | 97% |

More specifically, while the separation rate of Thr (threonine)—Ser (serine) is 89% by the conventional standard 30-minute analysis shown in FIG. 7, it is improved to 93% in this example. Also, while the separation rate of Gly (glycine)—Ala (alanine) is 95% by the conventional standard 30-minute analysis, it is improved to 97% in this example.

Stated otherwise, as is apparent from comparing FIGS. 8 and 7, this example makes it possible to speed up the standard assay to 15 minutes, and achieve higher separation rates than by the conventional standard 30-minute analysis.

Incidentally, as is apparent from comparison shown in Table 7, while the separation rate of Thr (threonine)—Ser (serine) is improved to 99% by the standard 20-minute analysis of Example 1, it is 93% in this example. Also, while the separation rate of Gly (glycine)—Ala (alanine) is improved to 100% by the standard 20-minute analysis of Example 1, it is 97% in this example. Thus, the separation rate in this example is lower than in Example 1.

This is a result of speeding up the buffer flow rate. In spite of a slight reduction, the separation rate in this example is still higher than in the prior art.

Furthermore, the comparison of FIGS. 8 and 6 shows that the height of each chromatogram peak in FIG. 8 representing this example is higher than in FIG. 6. This is because the time base is compressed from 20 minutes to 15 minutes. When the amino acid components are quantified by the chromatogram peak area method, the quantification accuracy is somewhat reduced as compared with Example 1 represented by FIG. 6, but not lower than in the conventional 30-minute analysis.

According to this example described above, the 15-minute analysis with the standard assay which has been infeasible heretofore can be achieved.

Also, the separation rate is improved as compared with the conventional standard 30-minute analysis.

Further, the load pressure of the separation column is lower than in the conventional standard 30-minute analysis and, therefore, the column life can be prolonged.

Next, a fifth example of the present invention will be described. In this example, the present invention is applied to the physiological fluid assay to achieve 60-minute analysis with the physiological fluid assay.

In this fifth example, too, an amino acid analyzer constructed as shown in FIG. 3 and a separation column having the structure as shown in FIG. 4 are used.

The analyzer body employs L-8500 model High Speed Amino Acid Analyzer by Hitachi. The separation column employs Ion Exchange Resin #2622-SC by Hitachi Custom. The particle size of this Ion Exchange Resin #2622-SC by Hitachi Custom is 3 μm. The ammonia filter column 8 employs Ion Exchange Resin #2650L by Hitachi Custom.

Analytical conditions are as shown in Table 8. For comparison, Table 8 also lists conditions of conventional 110-minute analysis with the physiological fluid assay.

TABLE 8

Analytical Conditions of Physiological Fluid Assay

| Item | Prior Art | Example 5 |
|---|---|---|
| Analyzing time (net) | 120 min | 60 min |
| Column size | 4.6 mmID × 60 mm | 6.0 mmID × 40 mm |
| Particle size of ion exchange resin | 3 μm | 3 μm |
| Buffer flow rate | 0.35 ml/min | 0.78 ml/min |
| Column linear speed | 21 mm/min | 27 mm/min |
| Column load pressure | 100 kgf/cm$^2$ | 110 kgf/cm$^2$ |
| Ninhydrin flow rate | 0.30 ml/min | 0.60 ml/min |
| Reaction coil size | 0.25 mmID × 7 m | 0.25 mmID × 7 m |
| Reaction coil linear speed | 13.3 m/min | 28.2 m/min |
| Reaction time | 0.53 min | 0.25 min |

Specifically, the separation column has the size of 6.0 mm inner diameter and 40 mm length as listed above. In other words, the separation column has a larger inner diameter and a shorter overall length than used in the conventional 30-minute analysis. The column size is the same as in Example 1. Further, in the separation column so sized, the ratio (L1/R) of the length L1 to the inner diameter R of the separation column is 6.6, i.e., not more than 10.

Also, the buffer flow rate is selected to 0.78 ml/min so that 60-minute analysis can be achieved with the physiological fluid assay. This value of the buffer flow rate is somewhat larger than (110/60) times the buffer flow rate (0.35 ml/min) in the conventional 110-minute analysis. The buffer flow rate is the same as in the standard 20-minute analysis of Example 1. The linear speed of the buffer flowing through the separation column is 27 mm/min in the 60-minute analysis with the physiological fluid assay and this value is a little higher than 21 mm/min in the conventional 110-minute analysis. However, since the inner diameter of the separation column is increased, the buffer flow rate can be raised and hence the analyzing time can be shortened. In addition, as to the column linear speed, the working limit linear speed is 36 mm/min as stated above and the value of 27 mm/min in this example is within the working limit linear speed.

Further, since the inner diameter of the separation column is also increased while the column linear speed is increased, the load pressure of the separation column becomes 110 kgf/cm$^2$; namely, it is a little higher than 100 kgf/cm$^2$ in the conventional 110-minute analysis. Comparing to an increase in the buffer flow rate, however, an increase in the load pressure of the separation column is suppressed. Thus, the life of the separation column is not so affected by a pressure rise in such an amount.

Corresponding to an increase in the buffer flow rate to 0.78 ml/min, the flow rate of the ninhydrin reagent is increased to 0.60 ml/min.

The reaction coil has the size of 0.25 mm inner diameter and 7 m length. Since a solution mixture of the buffer and the ninhydrin reagent flows through the reaction coil, an increase in both flow rates of the buffer and the ninhydrin reagent also increases the flow rate of the solution mixture. As a result, the linear speed of the solution mixture in the reaction coil is increased from 13.3 m/min to 28.2 m/min which satisfies the condition that it should be not less than 20 m/min.

Additionally, the value of $(r^4 \cdot L2)/f$ becomes $1.24 \times 10^{-3}$ (mm$^4 \cdot$m/(ml/min)) which satisfies the condition that it should be not more than $2.5 \times 10^{-3}$ (mm$^4 \cdot$m/(ml/min)). The spread σ* resulted in this case is 0.047 (min) (=2.8 (s)) which satisfies the condition that it should be not more than 0.067 (min) (=4 (s)).

Because of the increased linear speed of the solution mixture with the reaction coil size remained the same, the reaction time is shortened to 0.25 minute from 0.53 minute in the conventional 110-minute analysis. While this cutdown of the reaction time reduces sensitivity to some extent, such a lowering of sensitivity is not problematic from the practical point of view. This point will be described later in conjunction with a chromatogram resulted by the 60-minute analysis with the physiological fluid assay of this example.

The physiological fluid 60-minute analysis can be achieved as described above. But, what attention must be focused on in this connection is a separation rate. Even with speed-up of the analyzing time, the assay is not practicable if the separation rate is reduced. In this example, a satisfactory separation rate is ensured as described later.

The composition of each buffer employed in the physiological fluid 60-minute analysis of this example will now be described with reference to Table 9.

TABLE 9

Composition of Buffer for Physiological Fluid Assay

| Name | PF-1 | PF-2 | PF-3 | PF-4 | PF-RG |
|---|---|---|---|---|---|
| Buffer No. | 1 | 2 | 3 | 4 | 5 |
| Li concentration (N) | 0.09 | 0.225 | 0.721 | 1.00 | 0.20 |
| 1. Distilled water (approx.) | 700 ml | 700 ml | 700 ml | 700 ml | 700 ml |
| 2. Lithium citrate ($4H_2O$) | 5.73 g | 9.80 g | 8.79 g | 9.80 g | — |
| 3. Lithium chloride | 1.24 g | 6.36 g | 26.62 g | 38.15 g | — |
| 4. Citric acid ($H_2O$) | 19.90 g | 12.00 g | 11.27 g | 3.30 g | — |
| 5. Lithium hydroxide | — | — | — | — | 8.40 g |
| 6. Ethyl alcohol | 30.0 ml | 30.0 ml | 100.0 ml | — | 30.0 ml |
| 7. Thiodiglycol | 5.0 ml | 5.0 ml | — | — | — |
| 8. Benzyl alcohol | — | — | 3.0 ml | — | — |
| 9. BRIJ-35* | 4.0 ml | 4.0 ml | 4.0 ml | 4.0 ml | 4.0 ml |
| 10. pH (nominal) | 2.8 | 3.7 | 3.6 | 4.1 | — |
| 11. Total amount (measured) | 1.0 l | 1.0 l | 1.0 l | 1.0 l | 1.0 l |
| 12. Caprylic acid | 0.1 ml | 0.1 ml | 0.1 ml | 0.1 ml | 0.1 ml |

In Table 9, PF-1 represents the composition of the first buffer, PF-2 the composition of the second buffer, PF-3 the composition of the third buffer, PF-4 the composition of the fourth buffer, and PF-RG the composition of the column regenerating solution, respectively.

The first buffer FPF-1 has Li concentration of 0.09N and is prepared by dissolving, in distilled water of approximately 700 ml, lithium citrate ($4H_2O$) of 5.73 g, lithium chloride of 1.24 g, citric acid ($H_2O$) of 19.90 g, ethyl alcohol of 30.0 ml, thiodiglycol of 5.0 ml, BRIJ-35 of 4.0 ml and caprylic acid of 0.1 ml, and then further adding distilled water so that the total amount is 1.0 (1000 ml). The pH-value of the first buffer PF-1 is 2.8 (nominal).

The second buffer PF-2 has the same composition as the first buffer PF-1, but; its composition ratio is changed as shown in Table 7. Thus, the second buffer PF-2 has Li concentration of 0.225N and pH 3.7.

The third buffer PF-3 employs 3.0 ml benzyl alcohol instead of thioglycol which is employed in the first buffer PF-1, and has a composition ratio as shown in Table 7. Thus, the third buffer PF-3 has Li concentration of 0.721N and pH 3.6.

The fourth buffer PF-4 is deprived of ethyl alcohol and thioglycol from the first buffer, and has a composition ratio as shown in Table 7. The fourth buffer PF-4 has Li concentration of 1.00N and pH 4.1.

The regenerating solution RF-RG has Li concentration of 0.20N and is prepared by dissolving, in distilled water of approximately 700 ml, lithium hydroxide of 8.40 g, ethyl alcohol of 30.0 ml, BRIJ-35 of 4.0 ml and caprylic acid of 0.1 ml, and then further adding distilled water so that the total amount is 1.0 (1000 ml).

Then, an analysis program showing changeover timing and selection of the buffers for the physiological fluid 60-minute analysis of this example will be described with reference to Table 10.

TABLE 10

Analysis Program

| STEP | TIME (min) | BUFFER (TOTAL 100%) | | | | | COLUMN TEMP |
|---|---|---|---|---|---|---|---|
| | | V1 | V2 | V3 | V4 | V5 | |
| 1 | 0.0 | 100 | — | — | — | — | 38 |
| 2 | 2.0 | — | — | — | — | — | 31 |
| 3 | 10.0 | 100 | — | — | — | — | |
| 4 | 10.1 | 80 | 20 | — | — | — | |
| 5 | 11.0 | — | — | — | — | — | 58 |
| 6 | 16.8 | 70 | 30 | — | — | — | |
| 7 | 16.9 | 10 | 90 | — | — | — | |
| 8 | 17.5 | — | — | — | — | — | 40 |
| 9 | 22.0 | 10 | 90 | — | — | — | |
| 10 | 22.1 | — | 100 | — | — | — | |
| 11 | 23.0 | — | — | — | — | — | 70 |
| 12 | 25.0 | — | 100 | — | — | — | |
| 13 | 25.1 | — | — | 100 | — | — | |
| 14 | 34.5 | — | — | — | — | — | 45 |
| 15 | 35.5 | — | — | 100 | — | — | |
| 16 | 35.6 | 60 | — | — | 40 | — | |
| 17 | 38.5 | 60 | — | — | 40 | — | |
| 18 | 38.6 | — | — | — | 100 | — | |
| 19 | 44.0 | — | — | — | 100 | — | |
| 20 | 44.1 | — | 20 | — | 80 | — | |
| 21 | 48.0 | — | — | — | — | — | 70 |
| 22 | 52.0 | — | 20 | — | 80 | — | |
| 23 | 52.1 | — | — | — | 100 | — | |
| 24 | 57.5 | — | — | — | 100 | — | |
| 25 | 57.6 | — | — | — | — | 100 | |
| 26 | 63.0 | — | — | — | — | 100 | |
| 27 | 63.1 | 100 | — | — | — | — | 38 |
| 28 | 80.0 | 100 | — | — | — | — | |

Table 10 represents, from left to right, the step number, the run time (min) of each step, the flow rate of the buffer, and the temperature (°C.) of the separation column.

In the steps 1–3, i.e., during a period from 0.0 to 10.0 minutes, the electrovalve V1 for introducing the first buffer is driven so that the first buffer flows in 100%. The temperature of the separation column in this period is controlled to 38° C. at the time of 0.0 minute in the step 1 and then lowered to 31° C. at the time of 2.0 minutes in the step 2.

In the step 4, i.e., at the time of 10.1 minutes, the electrovalve V1 for introducing the first buffer and the electrovalve V2 for introducing the second buffer are driven so that the first and second buffers flow at a flow rate ratio of 80% and 20%, resulting in 100% in total. The electrovalves V1, V2 are each driven with the pulse width modulation. Thus, the flow rate ratio can be controlled by setting the opening angle of the electrovalve V1 to 80% and the opening angle of the electrovalve V2 to 20%, respectively, closing the electrovalve V2 at the timing at which the electrovalve V1 is opened, and conversely opening the electrovalve V2 at the timing at which the electrovalve V1 is closed. The temperature of the separation column at this time is also controlled to 31° C. In a period between the steps 3 and 4, the state of 100% first buffer is gradually changed into the state of 80% first buffer and 20% second buffer with a certain gradient.

In the steps 4–6, i.e., during a period from 10.1 to 16.8 minutes, the flow rate ratio between the first buffer and the second buffer is gradually changed with a certain gradient. Specifically, while in the step 4, i.e., at the time of 10.1 minutes, the electrovalve V1 for introducing the first buffer and the electrovalve V2 for introducing the second buffer are driven so that the first and second buffers flow at a flow rate ratio of 80% and 20%, resulting in 100% in total, the electrovalves are driven in the step 6, i.e., at the time of 16.8 minutes, so that the first and second buffers flow at a flow rate ratio of 70% and 30%, resulting in 100% in total. In this way, in the steps from 4 to 6, i.e., during the period from 10.1 to 16.8 minutes, the flow rate ratio between the first buffer and the second buffer is gradually changed with a certain gradient.

Also, in the intermediate step 5, i.e., at the time of 11.0 minutes, the temperature of the separation column is controlled to rise to 58° C.

In the steps 7–9, i.e., during a period from 16.9 to 22.0 minutes, the electrovalve V1 for introducing the first buffer and the electrovalve V2 for introducing the second buffer are driven so that the first and second buffers flow at a flow rate ratio of 10% and 90%, resulting in 100% in total. In a period between the steps 6 and 7, the state of 70% first buffer and 30% second buffer is gradually changed into the state of 10% first buffer and 90% second buffer with a certain gradient. Also, in the intermediate step 8, i.e., at the time of 17.5 minutes, the temperature of the separation column is controlled to 40° C.

In the steps 10–12, i.e., during a period from 22.1 to 25.0 minutes, the electrovalve V2 for introducing the second buffer is driven so that the second buffer flows in 100%. In a period between the steps 9 and 10, the state of 10% first buffer and 90% second buffer is gradually changed into the state of 100% second buffer with a certain gradient. Also, in the intermediate step 11, i.e., at the time of 23.0 minutes, the temperature of the separation column is controlled to 70° C.

In the steps 13–15, i.e., during a period from 25.1 to 35.5 minutes, the electrovalve V3 for introducing the third buffer is driven so that the third buffer flows in 100%. In a period between the steps 12 and 13, the state of 100% second buffer is gradually changed into the state of 100% third buffer with a certain gradient. Also, in the intermediate step 14, i.e., at the time of 34.5 minutes, the temperature of the separation column is controlled to 45° C.

In the steps 16–17, i.e., during a period from 35.6 to 38.5 minutes, the electrovalve V1 for introducing the first buffer and the electrovalve V4 for introducing the fourth buffer are driven so that the first and fourth buffers flow at a flow rate ratio of 60% and 40%, resulting in 100% in total. In a period between the steps 15 and 16, the state of 100% third buffer is gradually changed into the state of 60% first buffer and 40% fourth buffer with a certain gradient.

In the steps 18–19, i.e., during a period from 38.6 to 44.0 minutes, the electrovalve V4 for introducing the fourth buffer is driven so that the fourth buffer flows in 100%. In a period between the steps 17 and 18, the state of 60% first buffer and the 40% fourth buffer is gradually changed into the state of 100% fourth buffer with a certain gradient.

In the steps 20–22, i.e., during a period from 44.1 to 52.0 minutes, the electrovalve V2 for introducing the second buffer and the electrovalve V4 for introducing the fourth buffer are driven so that the second and fourth buffers flow at a flow rate ratio of 20% and 80%, resulting in 100% in total. In a period between the steps 19 and 20, the state of 100% fourth buffer is gradually changed into the state of 20% second buffer and 80% fourth buffer with a certain gradient. Also, in the intermediate step 21, i.e., at the time of 48.0 minutes, the temperature of the separation column is controlled to 70° C.

In the steps 23–24, i.e., during a period from 52.1 to 57.5 minutes, the electrovalve V4 for introducing the fourth buffer is driven so that the fourth buffer flows in 100%. In a period between the steps 22 and 23, the state of 20% second buffer and 80% fourth buffer is gradually changed into the state of 100% fourth buffer with a certain gradient.

In the steps 25–26, i.e., during a period from 57.6 to 63.0 minutes, the electrovalve V5 for introducing the regenerating solution is driven so that the column regenerating solution flows in 100%. In a period between the steps 24 and 25, the state of 100% fourth buffer is gradually changed into the state of 100% regenerating solution with a certain gradient. By introducing the column generating solution to flow through the separation column, the separation column is washed and regenerated.

In the steps 27–28, i.e., during a period from 63.1 to 80.0 minutes, the electrovalve V1 for introducing the first buffer is driven so that the first buffer flows in 100%. In a period between the steps 26 and 27, the state of 100% column generating solution is gradually changed into the state of 100% first buffer with a certain gradient. Also, in the step 27, i.e., at the time of 63.1 minutes, the temperature of the separation column is controlled to 38° C. By so letting the first buffer flow, the flow path line is filled with the first buffer to establish an equilibrium state in the separation column and, at the same time, the column temperature is controlled to the initial value, i.e., 38° C., for preparation of the next analyzing cycle.

Figure 9:
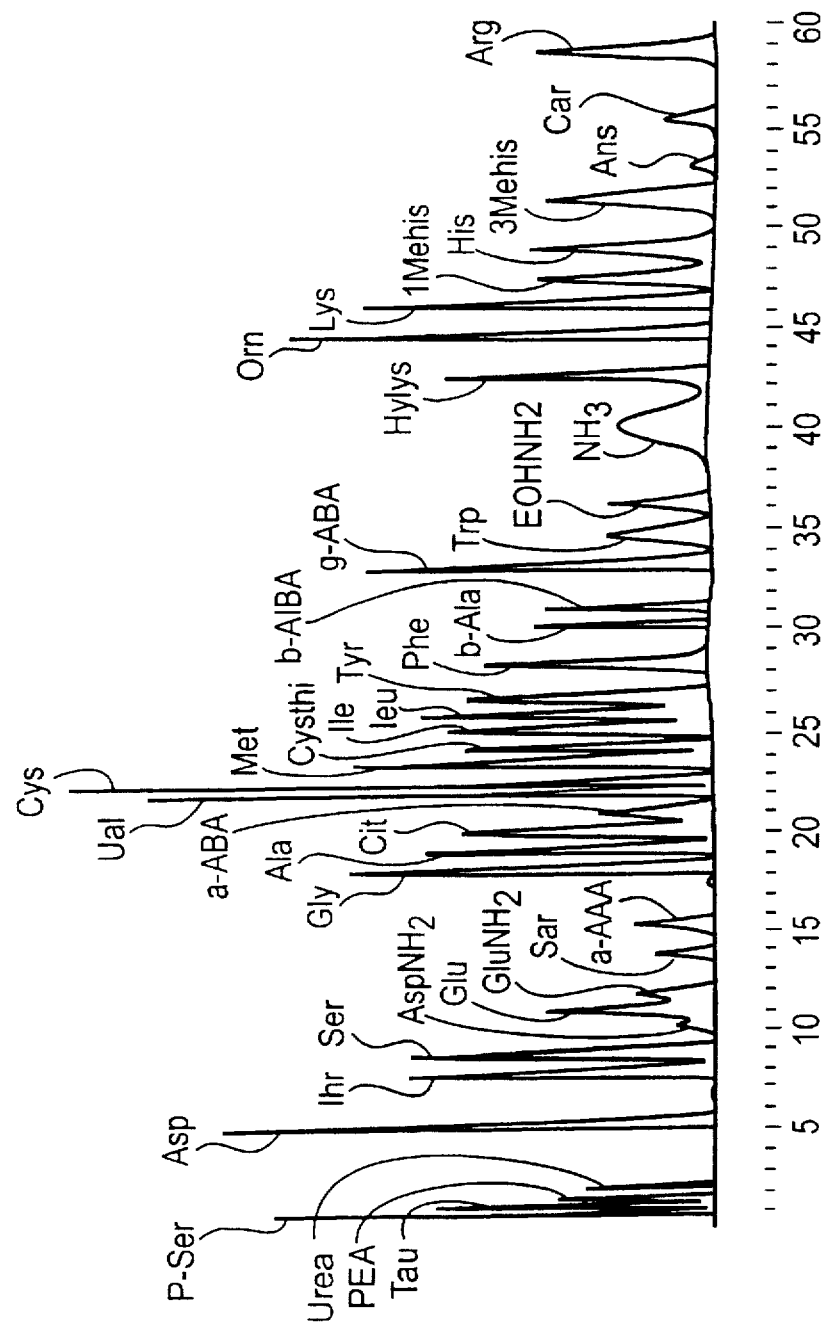
FIG. 9 is a chart showing a chromatogram resulting when a 20-minute analysis with the physiological fluid assay was carried out by using the amino acid analyzer according to one embodiment of the present invention.
Figure 10:
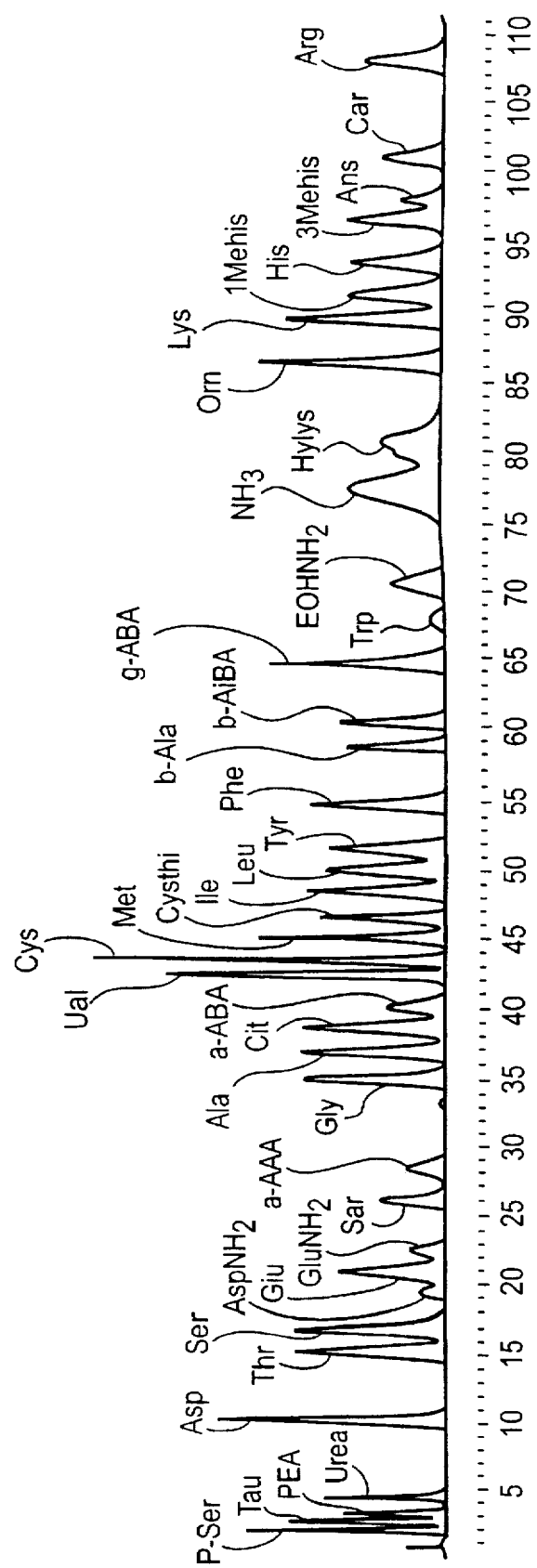
FIG. 10 is a chart showing a chromatogram resulting from a conventional 110-minute analysis with the physiological fluid assay.

FIG. 9 shows a chromatogram resulting when amino acid family materials of a physiological fluid contained in a standard sample were analyzed according to this example, and FIG. 10 shows a chromatogram resulted when the conventional 110-minute analysis with the physiological fluid assay was carried out on the same standard sample. The horizontal axis of each of FIGS. 9 and 10 represents time (min).

As seen from FIG. 9, the analysis of all the components is completed in 60 minutes. On the other hand, the conventional physiological fluid 110-minute analysis shown in FIG. 10 takes 110 minutes until completion of the analysis. Thus, according to this example, the analysis of all the components can be performed in 60 minutes, i.e., at a higher speed corresponding to about a half the analyzing time required in the prior art, with the physiological fluid assay.

As is apparent from comparing FIGS. 9 and 10, during a period from Asp (asparagic acid) to Ala (alanine), this example provides clearer separation between chromatogram peaks than in the prior art. As indices for representing a degree of separation between chromatogram peaks, there are generally employed a separation rate of Thr (threonine)—Ser (serine) and a separation rate of Gly (glycine)—Ala (alanine). Table 11 shows calculated separation rates of chromatogram peaks in FIGS. 10 and 11 for those separation rates as indices.

TABLE 11

Comparison of Separation Rates by Physiological Fluid Assay

|  | Prior Art | Example 5 |
|---|---|---|
| Thr—Ser | 96% | 98% |
| Gly—Ala | 98% | 99% |

While the separation rate of Thr (threonine)—Ser (serine) is 96% by the conventional physiological fluid 110-minute analysis shown in FIG. 10, it is improved to 98% in this example. Also, while the separation rate of Gly (glycine)—

Ala (alanine) is 98% by the conventional physiological fluid 110-minute analysis, it is improved to 99% in this example.

Stated otherwise, as is apparent from comparing FIGS. 9 and 10, this example makes it possible to speed up the physiological fluid standard assay to 60 minutes, and achieve higher separation rates than by the conventional physiological fluid 110-minute analysis.

Furthermore, the height of each chromatogram peak is somewhat higher in FIG. 9 representing this example. This is because the horizontal axis as the time base is compressed. Since the amino acid components under analysis are quantified by the chromatogram peak area method, the peak area is determined more precisely because of the improved separation rate of the chromatogram peak and hence clearer separation between two peaks. As a result, the measurement accuracy is not deteriorated in this example.

According to this example described above, the 60-minute analysis with the physiological fluid assay which has been infeasible heretofore can be achieved.

Also, the separation rate is improved as compared with the conventional physiological fluid 110-minute analysis.

Based on the foregoing examples, the present invention is briefed as follows.

It is thought that a working limit of the separation column depends not on the buffer flow rate, but the column linear speed. Therefore, the inner diameter of the separation column is increased as a method for raising the buffer flow rate and hence shortening the analyzing time without exceeding the limit in the column linear speed. In this connection, when the flow rate of the buffer flowing through the separation column of 4.6 mm inner diameter is 0.6 ml/min, the column linear speed is 36 mm/min.

As seen from the foregoing examples, by increasing the inner diameter of the separation column, it is possible to raise the buffer flow rate and hence shorten the analyzing time to 20 minutes with the standard assay, 15 minutes with the standard assay, and 60 minutes with the physiological fluid assay, thereby achieving higher speed analysis.

Also, if the particle size of the ion exchange resin is selected to be the same 3 μm as conventional for improving the column efficiency, a pressure loss in the column would be increased because of the small particle size. To reduce the pressure loss, therefore, the overall length of the separation column is shortened.

In other words, the inner diameter r of the separation column is increased and the overall length L1 thereof is shortened. Expressing this relationship in terms of (length L1/inner diameter r), the value L1/r is preferably not more than 10.

Further, the particle size of the ion exchange resin is preferably selected to be smaller for improving the column efficiency (increasing the number of theoretical stages). The particle size of the ion exchange resin is therefore selected to be not more than 4 μm. In addition, using fine particles of 4 μm or less brings about the above-stated phenomenon that a working limit of the separation column depends on the column linear speed.

As to the inner diameter of the separation column, when practicing the standard assay in 25 minutes instead of the conventional 30-minute, analysis, it is required to increase the inner diameter $(30/25)^2$. Because 4.6 m×$(30/25)^2$ is 5 mm, it is preferable that the inner diameter be not less than 5 mm.

Likewise, to achieve 15-minute analysis, it is required to increase the inner diameter to 6.5 mm theoretically. But 15-minute analysis is experimentally achieved with the inner diameter of 6 mm. If the inner diameter is further increased to 7 mm or more, the analyzing time would be sped up, but sensitivity would be deteriorated. Therefore, the practical range of the inner diameter is not less than 5 mm from the standpoint of high speed analysis, and not more than 7 mm from the standpoint of sensitivity. Thus, the inner diameter of the separation column is practically in the range of 5 mm to 7 mm.

When the overall length of the separation column is shortened and the number of theoretical stages is reduced, a spread of the sample zone outside the column becomes more likely to affect separation adversely. Considering contributions of parts upon the spread outside the column, it has been experimentally confirmed that the reaction coil is a flow path part which contributes to about 80% of the spread outside the column.

Here, assuming the spread of the sample zone in the reaction coil to be $\sigma$ and the spread in a unit of time to be $\sigma^*$, it is thought that if the spread $\sigma^*$ is made not more than 4 seconds, the spread is negligible from the separation point of view. Turning the unit of time into minute (min), the above condition is expressed such that the spread $\sigma^*$ should be not more than 0.067 min.

The spread $\sigma^*$ in Ea unit of time is a function of the inner diameter r of the reaction coil, the length L2 thereof, and the column flow rate. Therefore, the condition of $(r^4 \cdot L2)/f$ which is needed to make the spread $\sigma^*$ not more than 0.067 min is given below. Since the diffusion constant Dm is experimentally determined to be $1.20 \times 10^{-9}$ (m$^2$/s), that condition is given by that $(r^4 \cdot L2)/f$ is not more than $1.5 \times 10^{-7}$ (m$^2$/s). Using a unit generally used in the field of liquid chromatography, the condition is expressed such that $(r^4 \cdot L2)/f$ is not more than $2.5 \times 10^{-3}$ (mm$^4 \cdot$m/(ml/min)).

Further, the spread $\sigma^*$ in a unit of time is reduced as the flow rate f increases. In other words, when r and L2 are given with fixed values, the effect upon the spread $\sigma^*$ outside the column can be lessened by increasing the flow rate f.

The inner diameter r of reaction coils generally used is in series including 0.25 mm and 0.33 mm. Since the spread $\sigma^*$ in a unit of time is affected by fourth power of the inner diameter r, it is preferable that the inner diameter r be smaller. For this reason, the inner diameter r is selected to be not more than 0.25 mm.

The length L2 of the reaction coil is preferably longer for an improvement in sensitivity because the reaction time is prolonged correspondingly. However, if the length L2 of the reaction coil is increased, the spread $\sigma^*$ is enlarged. Taking into account the balance between such two contradictory features, the length L2 is selected to be not more than 10 m.

On condition that the inner diameter r and the length L2 of the reaction coil are selected respectively to be not more than 0.25 mm and 10 m, the flow rate f (ml/min) of the liquid flowing through, the column is determined to be not less than $2.5 \times 10^{-3}$ (ml/min). It is thus understood that the flow rate of the liquid flowing through the reaction coil should be selected to satisfy the above condition.

Here, by determining the linear speed of the liquid flowing through the reaction coil under the above condition, it is understood that the linear speed should be not less than 20 (m/min) when the inner diameter r of the reaction coil is 0.25 mm and the flow rate f of the liquid flowing through the column is $2.5 \times 10^{-3}$ (ml/min).

According to the present invention, it is possible, in a liquid chromatograph and chromatography, to perform a speeding up of an analyzing time, while mainting the column life and resolution.

What is claimed is:

1. A liquid chromatograph comprising a separation column, a pressurizing pump for feeding a mobile phase into said separation column, a sampler for mixing a sample into said mobile phase in a flow path upstream of said separation column, and a detector for detecting an effluent from said separation column, wherein the particle size of resin filled in said separation column is not more than 4 μm and a ratio (L1/R) of a length L1 (mm) to an inner diameter R (mm) of said separation column is not more than 10, and wherein the inner diameter R (mm) of said separation column is not more than 7 mm.

2. A liquid chromatograph according to claim 1, wherein the resin filled in said separation column is an ion exchange resin.

3. A liquid chromatograph according to claim 1, wherein the effluent from said separation column is reacted with a reaction solution.

4. A liquid chromatograph according to claim 1, wherein the inner diameter R (mm) of said separation column is not less than 5 mm.

5. A liquid chromatograph comprising a separation column, a pressurizing pump for feeding a mobile phase into said separation column, a sampler for mixing a sample into said mobile phase in a flow path upstream of said separation column, a detector for detecting an effluent from said separation column, a reaction coil disposed in a flow path extending from said pressurizing pump to said separation column or a flow path extending from said separation column to said detector for reacting the effluent with a reaction solution, where when the inner diameter of said reaction coil is r (mm), the length of said reaction coil is L2 (m), and the flow rate of a liquid flowing through said reaction coil is f (ml/min), $(r^4 \cdot L2/f)$ is selected to be not more than $2.5 \times 10^{-3}$.

6. A liquid chromatograph according to claim 5, wherein the inner diameter r (mm) of said reaction coil is not more than 0.25 mm and the flow rate f (ml/min) of the liquid flowing through said reaction coil is not less than 1.0 ml/min.

7. A liquid chromatograph comprising a separation column, a pressurizing pump for feeding a mobile phase into said separation column, a sampler for mixing a sample into said mobile phase in a flow path upstream of said separation column, and a detector for detecting an effluent from said separation column, wherein the particle size of resin filled in said separation column is not more than 4 μm and the linear speed of a liquid flowing through said separation column is selected to be not more than 36 mm/min.

8. A liquid chromatograph comprising a separation column, a pressurizing pump for feeding a mobile phase into said separation column, a sampler for mixing a sample into said mobile phase in a flow path upstream of said separation column, and a detector for detecting an effluent from said separation column, wherein the particle size of resin filled in said separation column is not more than 4 μm and the flow rate of a liquid flowing through said separation column is set so that the analyzing time taken by the standard assay for amino acid analysis is not longer than 20 minutes.

9. A liquid chromatography comprising the steps of pressuring a mobile phase by a pressurizing pump, mixing a sample in said pressurized mobile phase, separating a solution mixture of said mobile phase and said sample in said separation column, and detecting an effluent from said separation column, wherein the particle size of resin filled in said separation column is selected to be not more than 4 μm and a ratio (L1/R) of a length L1 (mm) to an inner diameter R (mm) of said separation column is selected to be not more than 10 and wherein the inner diameter R (mm) of said separation column is not more than 7 mm.

* * * * *